(12) United States Patent
Kaufman et al.

(10) Patent No.: US 8,085,388 B2
(45) Date of Patent: Dec. 27, 2011

(54) LASER RADAR PROJECTION WITH OBJECT FEATURE DETECTION AND RANGING

(75) Inventors: Steven P. Kaufman, Hooksett, NH (US); Arkady Savikovsky, Burlington, MA (US); Christopher C. Chagaris, Manchester, NH (US); Joel Stave, New Boston, NH (US)

(73) Assignee: Laser Projection Technologies, Inc., Londonderry, NH (US)

( * ) Notice: Subject to any disclaimer, the term of this patent is extended or adjusted under 35 U.S.C. 154(b) by 681 days.

(21) Appl. No.: 12/001,606

(22) Filed: Dec. 11, 2007

(65) Prior Publication Data

US 2008/0246943 A1    Oct. 9, 2008

Related U.S. Application Data

(63) Continuation-in-part of application No. 11/345,784, filed on Feb. 1, 2006, now Pat. No. 7,306,339.

(60) Provisional application No. 60/649,241, filed on Feb. 1, 2005.

(51) Int. Cl.
*G01C 3/08* (2006.01)
(52) U.S. Cl. ....... 356/5.01; 356/4.01; 356/5.1; 356/5.15
(58) Field of Classification Search ........ 356/3.01–3.15, 356/4.01–4.1, 5.01–5.15, 6–22, 28, 28.5
See application file for complete search history.

(56) References Cited

U.S. PATENT DOCUMENTS

| | | |
|---|---|---|
| 5,090,804 A | 2/1992 | Wong et al. |
| 5,196,900 A | 3/1993 | Pettersen |
| 5,341,183 A | 8/1994 | Dorsey-Palmateer |
| 5,381,258 A | 1/1995 | Bordignon et al. |
| 5,416,591 A | 5/1995 | Yoshimura et al. |
| 5,436,027 A | 7/1995 | Offer |

(Continued)

FOREIGN PATENT DOCUMENTS

DE    3301 494 A1    7/1984

(Continued)

OTHER PUBLICATIONS

U.S. Appl. No. 10/492,264, Kaufman et al.

(Continued)

*Primary Examiner* — Thomas Tarcza
*Assistant Examiner* — Luke Ratcliffe
(74) *Attorney, Agent, or Firm* — Finch & Maloney PLLC

(57) ABSTRACT

A 3D pulsed laser projection system scans an object to produce a dense 3D point cloud and projects a laser light beam onto an object as a glowing template. A high-sensitivity optical feedback system receives and detects a feedback beam of the output beam light diffusely reflected from the object. The feedback light and projected beam share the same beam path between steering mirrors and the object. A light suppression component controls stray scattered light, including ambient light, from being detected. A time-of-flight measurement subsystem provides a distance-to-object measurement for projected pulses. An acousto-optical modulator, variable gain detected signal amplification and variable photo-detector power together produce a dynamic range for detected reflected feedback signals of at least 100,000, and up to 500,000. Optical fiber cables spatially filter scattered light and isolate the photo-detectors thermally. The laser is preferably pulsed at least 50 kHz, with sampling of the projected and feedback reflected optical pulse signals at a sampling rate of up to 10 gigasamples per second.

20 Claims, 15 Drawing Sheets

U.S. PATENT DOCUMENTS

| | | |
|---|---|---|
| 5,450,147 A | 9/1995 | Dorsey-Palmateer |
| 5,559,334 A | 9/1996 | Gupta et al. |
| 5,615,013 A | 3/1997 | Rueb et al. |
| 5,646,859 A | 7/1997 | Petta et al. |
| 5,651,600 A | 7/1997 | Dorsey-Palmateer |
| 5,663,795 A | 9/1997 | Rueb |
| 5,671,053 A | 9/1997 | Wigg et al. |
| 5,889,582 A | 3/1999 | Wong et al. |
| 5,894,123 A | 4/1999 | Ohtomo et al. |
| 5,956,143 A * | 9/1999 | Kotidis ............... 356/502 |
| 5,957,559 A | 9/1999 | Rueb et al. |
| 5,988,862 A | 11/1999 | Kacyra et al. |
| 6,024,449 A | 2/2000 | Smith |
| 6,036,319 A | 3/2000 | Rueb et al. |
| 6,044,170 A | 3/2000 | Migdal et al. |
| 6,066,845 A | 5/2000 | Rueb et al. |
| 6,246,468 B1 | 6/2001 | Dimsdale |
| 6,304,680 B1 | 10/2001 | Blake et al. |
| 6,365,221 B1 | 4/2002 | Morton |
| 6,547,397 B1 | 4/2003 | Kaufman et al. |
| 6,847,462 B1 | 1/2005 | Kacyra et al. |
| 6,935,748 B2 | 8/2005 | Kaufman et al. |
| 7,215,430 B2 | 5/2007 | Kacyra et al. |
| 2005/0007562 A1 | 1/2005 | Seki et al. |
| 2005/0035943 A1 | 2/2005 | Kojima |
| 2005/0082262 A1 | 4/2005 | Rueb et al. |
| 2005/0088644 A1 * | 4/2005 | Morcom ............... 356/10 |
| 2005/0121422 A1 | 6/2005 | Morden et al. |
| 2006/0170870 A1 | 8/2006 | Kaufman et al. |

FOREIGN PATENT DOCUMENTS

| | | |
|---|---|---|
| EP | 1 288 754 A2 | 3/2003 |
| WO | WO-03/032129 A2 | 4/2003 |
| WO | WO-2006/104565 A2 | 10/2006 |

OTHER PUBLICATIONS

"Update: Automated repair," High Performance Composites, www.compositesworld.com. (Mar. 2007), pp. 34-36.

* cited by examiner

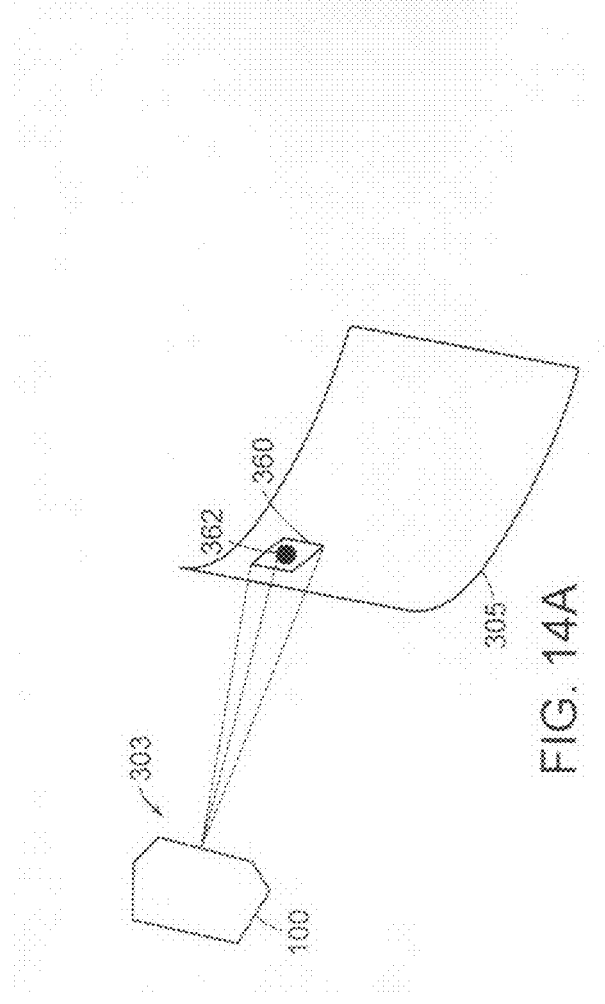
FIG. 14A
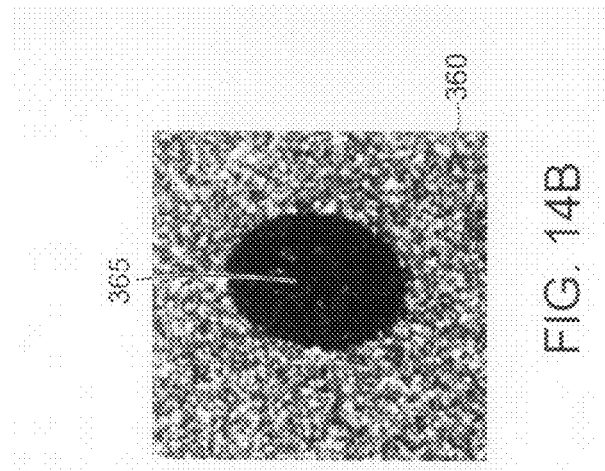
FIG. 14B
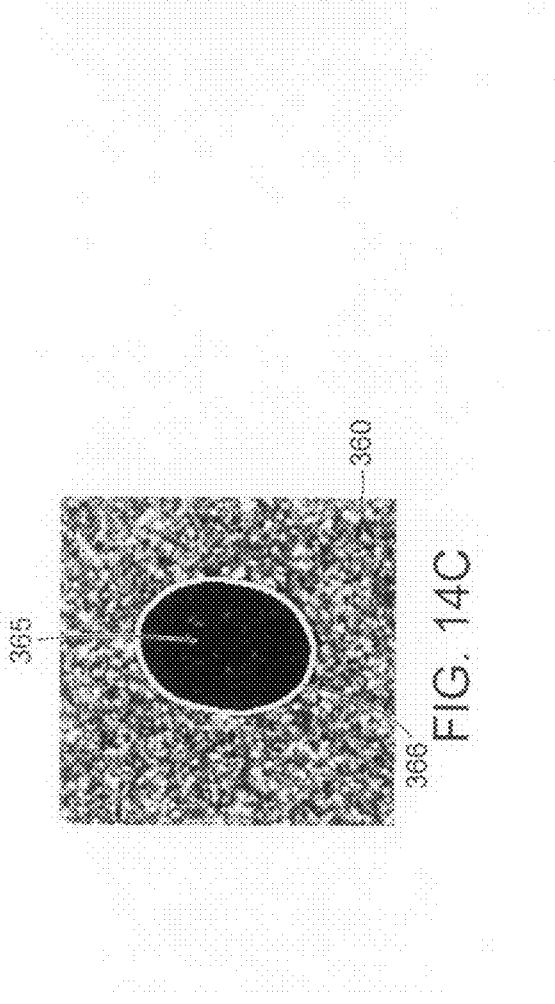
FIG. 14C
FIG. 14D

LASER RADAR PROJECTION WITH OBJECT FEATURE DETECTION AND RANGING

CROSS-REFERENCE TO RELATED APPLICATIONS

This application is a continuation-in-part of, and claims priority under 35 USC 120 of, U.S. patent application Ser. No. 11/345,784 filed Feb. 1, 2006 issuing Dec. 11, 2007 as U.S. Pat. No. 7,306,339, the disclosure of which is incorporated herein by reference, and also claims priority under 35 USC 119(e) of U.S. Provisional Patent Application No. 60/649,241 filed on Feb. 1, 2005, the disclosure of which is also incorporated herein by reference.

FIELD OF THE INVENTION

This invention relates to laser projection systems, and in particular to a laser projection system that projects a glowing template light pattern on an object without requiring retro-reflective or cooperative targets and provides 3D location and light reflectivity information about points on the object to pixels with high precision, sensitivity, and dynamic range.

BACKGROUND OF THE INVENTION

Laser projectors are widely used in manufacturing processes to assist in precision assembly of large scale structures, composite articles, etc. in aerospace, construction and other industries. Laser projectors are distinguished from digitizing scanners. U.S. Pat. No. 6,246,468 to Dimsdale is one example of a laser scanner that uses pulsed laser light to determine range to points on an object and create a point cloud of image data points In the Dimsdale system, a separate video system gathers information about the intensity of the reflected light.

Known laser projectors use a scanned output beam of a continuous wave laser to generate glowing templates on a 3D object surface utilizing computer assisted design (CAD) data for projection trajectories. Typically laser projectors include optical feedback to assist in defining projector's location and orientation in 3D space with respect to the object's coordinate system. This defining is commonly termed "bucking in." It requires use of several, typically three to six, reference (fiducial) points selected or placed on or about the work surface of the object. One specific example of this type of laser projector, for example, is disclosed in U.S. Pat. No. 5,450,147 to Palmateer. The '147 laser projector system uses a plurality of cooperative reference targets mounted, on or adjacent to, the object. These targets return the laser light back into the projector's beam steering system. Another laser projector disclosed in U.S. Pat. No. 5,381,258 to Bordignon specifically requires reference targets to be retro-reflective. Yet another laser projector described in Kaufman and Savikovsky U.S. Pat. No. 6,547,397 issued to two of the present inventors relies on reference targets for both distance ranging and angle measurement.

The requirement to place reference targets onto the object has many practical drawbacks to the process of using laser projectors. It is time and labor consuming. It also degrades precision and reliability due to a lack of precision in the placement and resultant position of the target Some potentially viable applications currently cannot be implemented because they do not allow any target placement on the object surface.

The main reason retro-reflective reference targets are used in almost all laser projecting systems is because they provide quite distinguishable optical feedback signal by returning a substantial portion of projected laser light back into the beam path through the beam steering system.

The maximum output laser beam power allowed for laser projectors due to laser safety regulations is 5 milliwatts. The power of the portion of the laser light that is reflected from a typical retro-reflective target and directed back through the beam steering system is typically about 200 to 1,000 nanowatts depending on the distance between projector and a target and on the size of the beam steering mirrors.

A number of solutions are proposed in the prior art to deal with the problem of the optical feedback using the same beam path through the beam steering system as the output projector beam. They involve different ways to separate the output laser beam from the received feedback light in the laser projector. The aforementioned Palmateer '147 patent utilizes a beam splitter. The Bordignon '258 patent teaches using a particular wedge-shaped lens with a central opening for the output beam. Laser projectors in Kaufman and Savikovsky '397 patent use a reflective optical pick-up prism. Each of these solutions provides somewhat different effectiveness of utilizing received feedback light that is directed toward a photo detector. Using retro-reflective targets and these known solutions to the problems of a shared optical path, typical optical feedback beams that reaches the photo detector are estimated at 50 to 500 nanowatts of power.

It is very desirable in laser projection to use the object features (e.g., corners, holes, fasteners, etc.) as fiducial points for laser projection instead of separately placed retro-reflective targets. However, prior attempts to solve this problem have not provided a solution without other drawbacks. For example, U.S. Pat. No. 5,615,013 to Rueb offers a solution combining a galvanometer and a camera system. A serious drawback of the Rueb arrangement is the existence of two different optical paths for laser projection and camera imaging, which necessitates for frequent mutual calibration between the camera imaging system and the laser projection system. It is necessary to use separate reference targets in the process of this mutual calibration. As a result, the suggested solution reduced accuracy.

In order to maintain a high level of laser projection precision (e.g. to within ±0.015 inch at a laser-to-object distance of 15 feet), it is required that the beam path through the beam steering system is the same for both the optical feedback and the output projector beam. However, if retro-reflective targets are not used, the power level of light diffusely reflected back from a typical object material like plastic or painted metal, and returned through the projector beam steering system, has been determined to be about 1,000 times less than the reflected light power from a typical retro-reflective target. That means the typical optical feedback beam that reaches a photo detector is roughly in the range of 50 to 500 picowatts of power. In other words, the typical optical feedback beam power from the non-target object feature that reaches the photo detector is about 100 million times less than the output laser projector beam power. Because the output beam has to share the optical path with the feedback beam it adds prevailing, unwanted background light due to the light scatter and secondary reflections. This unwanted "stray" light renders the optical feedback signal undistinguishable.

In a conventional laser projection application for product assembly, once all the known fiducial points have been detected, a laser projector's computer runs mathematical algorithm to calculate precise position and orientation of the laser projector with respect to the object. Then it starts actual projection. It generates a series of beam steering commands in a precisely arranged way to direct the beam at each given moment of time exactly toward the given trajectory CAD point (x, y, z) on the surface of the 3D object. The beam strikes the surface of the object following the computer-controlled trajectory in a repetitive manner. With sufficiently high beam speed, the trajectory of the projected beam on the object's surface appears to human eye as a continuous glowing line.

Glowing templates generated by laser projection are used in production assembly processes to assist in the precise positioning of parts, components, and the like on any flat or curvilinear surfaces. Presently laser projection technology is widely used in manufacturing of composite parts, in aircraft and marine industries, or other large machinery assembly processes, truss building, and other applications. It gives the user ability to eliminate expensive hard tools, jigs, templates, and fixtures. It also brings flexibility and full CAD compatibility into the assembly process.

In the laser assisted assembly process, a user positions component parts by aligning some features (edges, corners, etc.) of a part with the glowing template. After the part positioning is completed, the user fixes the part with respect to the article being assembled. The person assembling the article uses his or her eyesight to make a judgment about proper alignment of the part to the glowing template. Because this process relies on the visual judgment of a worker, it is subjective, and its quality may be substantially reduced by human errors.

Human errors adversely impact any manufacturing process, they are unacceptable, and they have to be revealed as soon as possible. In aircraft manufacturing, for example, every production step has to be verified and properly documented. One hundred percent quality assurance is often required. Therefore, a device and method that combines the capabilities of laser projection with immediate verification of part placement during assembly process are very desirable. They would provide the benefits of revealing and fixing human errors right on the spot, thus avoiding very costly and time-consuming off-line testing procedures.

Existing 3D laser projectors use design model CAD data to generate glowing templates on a 3D object surface. Hence, precision of the laser projection is adequate only if the object is build exactly up to its model.

There is therefore a great need for an effective way to deliver an optimized 3D laser projection on the surface of the object that differs from its design model. For example, US Patent Application 2005/0121422 A1 discloses a technical solution based on sequential use of a separate 3D digitizing system, first, to determine as-built condition of the object, then, second, to modify as-design data for laser projection utilizing results of digitizing, and then, third, using a separate 3D laser projector to generate a glowing template. This system is complicated, requires use of a cage with retro-reflective targets and requires sequential usage of two separate expensive units of equipment—digitizer and projector. Because of the need to use multiple units and multiple operations, this system is limited in its accuracy, particularly the high precision required for modern aircraft and other precision manufacturing, e.g. to ±0.015 inch at 15 feet.

Another example—an industrial process for an aircraft composite component diagnostics/repair—is disclosed in the article "Update: Automated Repair" in High-Performance Composites, March 2007, pp. 34-36. Again, this solution requires separate sequential use of two very different and expensive units of equipment –3D digitizing system and 3D laser projector.

Hence, there is a need for a laser projector with full 3D digitizing capabilities, including ability to detect object features.

Known solutions for stand alone 3D scanning digitizers are not suitable for laser projection with feature detection. For example, the Laser Radar LR200 manufactured by Metris utilizes a large gimbal-mounted mirror for beam steering and an infrared laser for distance measurement. This system, however, is quite slow and it cannot generate glowing templates as a laser projector.

A 3D scanning digitizer with a time-of-flight ranging system is disclosed as one embodiment in U.S. Pat. No. 7,215,430. It utilizes a pulsed "green" laser with a relatively low repetition rate, an avalanche photodiode as a detector, and a threshold-based timing circuit. This solution relies on separate video cameras to obtain an image of the object. It cannot provide required accuracy for the high precision edge features detection. Also, the described system does not capture signals returned from objects well if they have a substantially variable reflectivity. For such objects this system obtains very sparse data with low spatial resolution. Again, the disclosed apparatus is only a digitizer; it cannot effectively generate glowing templates for laser projection.

The dynamic range of a digitizer in dealing with variations in the intensity of light returned from a scanned object is a serious practical limitation on the usefulness of known digitizers. Scanning a white wall versus scanning a black wall can produce 100× variations in the reflected light intensity. A white wall scanned at a distance of six feet produced a variation of roughly 3,000× compared to a black object at 40 feet distance. A polished steel ball is a particularly difficult object to scan because it produces basically a strong single point reflection surrounded by much weaker reflections. A versatile 3D digitizing scanner and projector should have a dynamic range of 100,000 to 500,000 to work with a wide variety of objects and in a wide variety of operating conditions encountered in practical applications. Known scanners and known projectors do not provide anywhere near this dynamic range.

A laser projector solution capable of distance ranging is described in the aforementioned Kaufman and Savikovsky U.S. Pat. No. 6,547,397. However, as noted above, it works only with retro-reflective reference targets (surfaces). Moreover, it does not provide adequate sensitivity and dynamic range to accurately acquire a variety of conventional surfaces and 3D objects and to detect their edge features. It projects a glowing template using a continuous wave laser. In ranging to orient the projector to a workpiece, it uses a pulsed laser beam, but one pulsed at the maximum rate near 1 kHz. Distance information for all pixels corresponding to the scanned pulses cannot be obtained.

It is therefore a principal object of this invention to provide a laser projector that can also scan an object as a 3D digitizer that produces a dense point 3D cloud through a combination of distance ranging capability with the angular scan and feature detection capability that distinguishes very weak optical feedback signal returned from any object surface in the presence of the relatively powerful output projector beam and the ambient light with a sufficiently high sensitivity to the optical feedback.

Another object of this invention is to provide a solution for obtaining x, y, z point cloud and intensity data with high spatial resolution to adequately extract detailed information about scanned 3D objects needed for high precision laser projection such as used in aircraft manufacture.

Still another object of this invention is to provide a laser radar projector capable of adequately capturing signals from a wide variety of surfaces with very different reflectivity belonging to the same scan scene.

A further object of this invention is to provide such a laser radar projector that can generate a glowing template consisting of fixed dots with a sufficiently small separation between them to produce a workable projected glowing template on the object.

SUMMARY OF THE INVENTION

A 3D laser scanner and projection system both produces a dense, precise 3D digital image of an object surface and scans a glowing template into the object. The system can detect features on, and range to points on the surface of an object. The features can serve as fiducial points for targetless operation. Because of the distance determining capablity, the system is also termed herein a laser radar projector ("LRP") or targetless laser radar projector ("TLRP"). The 3D laser scanner and projection system can project a glowing template precisely positioned on an object as it actually exists, not on the object as it is modeled in a CAD program or the like.

In one form the TLRP of this invention includes a laser projector that projects a pulsed laser light beam on the surface and scans the pulsed output beam along a beam path over the surface where a portion of said output light is diffusely reflected from the surface back to the projector as a feedback signal light beam. A first optical signal detector at the laser projector receives the feedback signal light beam and converts it into a digital image signal that corresponds to the detected feedback signal light. A suppression system controls stray light reaching the optical detector that would prevent the detection of said feedback signal. The projected light beam and the feedback signal light beam associated with a given point on the surface propagate in opposite directions along the same projected beam path. A time-of-flight measuring system calculates the elapsed time of flight and distance traveled of pulses from the laser, to points on the object surface, and back via said signal light feedback beam to the detector.

The TLRP has a high-sensitivity optical feedback from a scanned object shares the beam path of the laser output beam, through the beam steering system to the object, with the output projecting beam. The TLRP separates the output beam and the optical feedback beam while substantially suppressing unwanted prevailing background light, including the ambient light illuminating the object, from reaching a photodetector for the feedback beam. Because the optical feedback is time delayed with respect to its associated reference pulse in the present TLRP invention, the scattering generated by the output beam is out of synch with the optical feedback. This provides a degree of inherent control over the adverse impact of the scattered light on the detection of the very faint optical feedback signal pulses. The separation of the optical feedback, both optically and in time, together with other stray and scattered light suppression systems described herein, makes the weak optical feedback signal from a typical object feature distinguishable enough to enable usage of object features as fiducial points for laser projection, thereby providing the targetless laser projection.

The TLRP has a computer that converts the optical feedback scan signal from the photodetector into a digital image. It processes the image to determine object features locations with respect to the projector coordinate system. The TLRP computer also defines the projector location and orientation in 3D space with respect to the object based on the optical feedback scan data from the object's features.

The TLRP time of flight measurement system includes a beam splitter located in the beam path that divides the projected pulsed laser light beam into a reference beam portion and a signal beam portion. A second reference optical detector converts the reference beam portion into a corresponding electrical reference signal.

A lens focuses the reference beam portion onto the second reference optical detector. A computer compares the digital image signals with the corresponding electrical reference signals to produce a measurement of the distance from the TLRP to the a point on the object surface that produces the feedback signal light beam. The time of fight measurement system further includes an electronic circuit that samples the reference signal and the digital image signal at a rate sufficient to provide accurate values for the elapsed time of flight to the point on the object surface. The laser beam is pulsed at least 50 kHz and the sampling occurs at least 5 gigasamples per second. Preferably, the pulse rate is about 100 kHz and the sampling rate is about 10 gigasamples per second. A master clock synchronizes the operation of the laser, the sampling circuit, the computer, and the scanning.

To provide accurate 3D information about points on a wide variety of objects under a wide range of operation conditions, the TLRP has a dynamic range modulator that adjusts the operation of the TLRP in response to the light reflective characteristics of the object being scanned and projected upon. The dynamic range variation is on the order of at least 100,000, but preferably is near 500,000. The dynamic range modulator includes an acousto-optical modulator located in the pulsed output beam and preferably operable to vary the intensity of the pulsed output beam over a range from 1 to 300 to 500. This acousto-optical modulator splits the pulsed output beam into a first order beam of pulses and a zero order beam of pulses, where the first order beam is scanned on the object and the zero order beam is suppressed, e.g. by a blocking plate positioned in the beam path. The dynamic range modulator further includes a variable gain amplifier of the digital image signal output by the first optical signal detector, and a variable power supply for the optical feedback signal detector that varies its sensitivity to said received feedback signal light beam.

The TLRP preferably 3D optically couples to the photodetectors to the system by optical fibers that thermally isolate the detectors from heat produced by the computer or other electronics.

In the TLRP invention, the light suppression system includes a spatial light filter that admits the feedback light beam to the photodetector while substantially blocking stray light. In one form, the spatial filter uses, in part, an optical fiber with a central light-conducting core aligned with the optical detector. A converging lens brings the feedback light beam to a focus at one end of the central light receiving core.

To orient the TLRP to an object without retro-reflective targets, the TLRP scans different object features, such as corners, holes or other fabricated features, edges, and fasteners, to obtain spatial coordinates of those features with respect to the TLRP's coordinate system. While in essence a targetless system, as needed, the projector can also scan retro-reflective cooperative targets mounted on the object, as one type of the object features The invention also includes a method for assembling component parts with precision placement and fabrication processing and verification in space, onto and/or supported by an object. This method includes projecting a scanned pulsed laser light beam onto the object. The pulsed output beam is formed into a signal channel portion that is projected onto the object and a reference channel portion that is not projected onto the object. The method also includes selecting features on the object before assembly, where the fabrication or verification selecting includes creating a scan box around a selected feature, The projected light beam is scanned within the scan box. Light is diffusely reflected back from said object along said scanned laser light beam signal portion. Other light such as stray or internally scattered light is suppressed from entering the detector except for the feedback light, A digital image of the features and/or points on the object are created as a dense 3D digital image from the detected feedback light. This creating includes coupling the time of flight of a pulse of said signal channel portion light beam to the corresponding pulse in the reference channel portion to provide projection-to-object range information for scanned object points. The method can also include calculating fiducial points from the, features, calculating from plural fiducial points on the object the relative position and orientation of the source of the projecting and the object, and projecting a glowing template on the object that guides the assembly of the parts or fabrication processing or verification on or to the object.

The invention also includes a method of assembly a structure in 3D space with verification of the placement of component assembled parts and fabrication process steps on the object. The assembly process includes steps of generating glowing templates, placing component parts in 3D space, and verifying real locations of placed component parts against nominal design parameters by scanning their features. More specifically, this process includes providing a laser projector with high-sensitivity optical feedback capable of scanning features of a part and/or fabrication processing step after it has been positioned during the assembly and/or fabrication of an article to convert the optical feedback scan signal into a digital image, image processing to determine the part or fabrication features locations with respect to projector's coordinate system, and computing to verify the location of the placed part and/or fabrication with respect to nominal (e.g., CAD) design parameters.

These and other features and objects of the invention will be more fully understood from the following detailed description of the invention which should be read in light of the accompanying drawings.

BRIEF DESCRIPTION OF THE DRAWINGS

FIG. 14A is a view corresponding to FIGS. 13A and 13B showing a circular hole ("dot") object feature within the object;

FIGS. 14B-D are views corresponding to FIGS. 13C and 13D showing the circular dot feature as imaged by the laser system, including a scan box (FIG. 14B), a feature edge detected (FIG. 14C), and a center reference point established (FIG. 14D);

DETAILED DESCRIPTION OF THE INVENTION

Targetless Object Feature Detection

Figure 1:
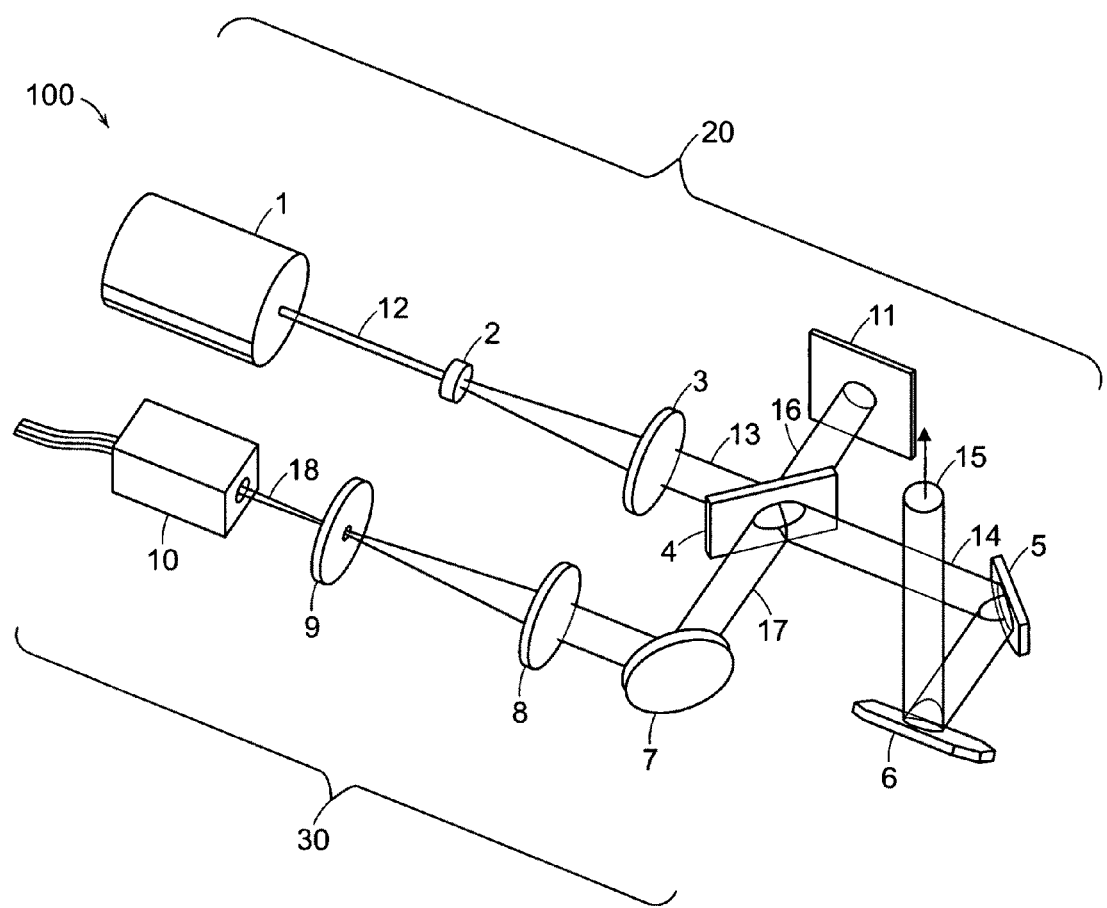
FIG. 1 is a simplified view in perspective of a laser projector capable of feature detection in the present invention.

FIGS. 1-15 relate to a targetless laser projector ("TLP") 100 as shown and described in Applicants' parent application referenced above. The laser radar projector ("LRP") 100R of the present improvement invention is described below with reference to FIGS. 16-18. The TLP 100 has two major optical subsystems—a projection subsystem 20 and an optical feedback subsystem 30. The projection subsystem 20 includes a laser 1, beam expanding lenses 2 and 3, a beam splitter 4, a beam dump 11, and beam steering mirrors 5 and 6. The beam steering mirrors are mounted on shafts of corresponding galvanometers 203, 204 in FIG. 6, as is well known in the laser projection art. The optical feedback subsystem 30 includes a mirror 7, a focusing lens 8, a spatial filter 9, and a high-sensitivity photo detector 10.

The laser 1 emits a laser beam 12. The laser 1 is typically a solid state diode pumped laser that produces light at the "green" wavelength of 532 nanometers. The power of the beam 12 output by the laser is preferably not more than 5 milliwatts, the upper power limit for class IIIa lasers, and is a continuous wave (cw) output. (This is in contrast to the laser 1P light source in the TLRP 100R described below where the output laser light beam is pulsed at a high rate.) The cw beam 12 has a typical diameter of about 0.4 to about 1.0 millimeter. Lenses 2 and 3 expand the beam 12 as it goes through them preferably about 10 to 15 times. The combination of lenses 2 and 3 also functions as the beam collimator so that the expanded beam 13 has about 10 to 15 times less divergence than the beam 12. The beam 13 then passes through the beam splitter plate 4 of known design. One part of the beam 13 reflects from the beam splitter 4 shown as beam 16, toward the beam dump 11. Another part of the beam 13 passes through the beam splitter 4 along the same direction as beam 14 directed toward the beam steering mirrors 5 and 6, in that order. The beam 15 that reflects from the second steering mirror 6 is directed toward the object of projection (e.g. object 105 in FIG. 5).

The object is typically a work piece formed of a solid material, a composite of materials, or an assembly of parts and/or materials. In a typical aerospace application, the object is an aircraft, or a part of an aircraft. The object, at least in part, diffusely reflects light. It can, however, strongly reflect light, e.g. from polished, convexly curved, or glossy painted surface or surfaces. The object can be a liquid, e.g. as in a wet coating of paint or adhesive. However, the object is normally a solid, is diffusely reflective, and has no retro-reflective targets mounted thereon.

Figure 2:
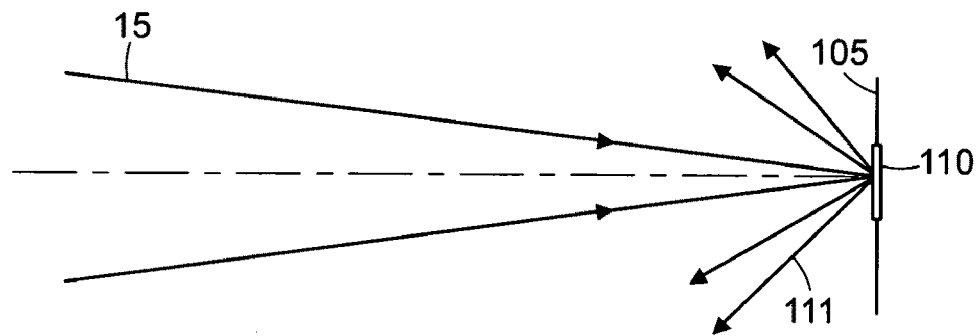
FIG. 2 is a simplified detail view in cross-section of the projected laser beam from the projector shown in FIG. 1 striking the outer surface of an object and being diffusely reflected.
Figure 3:
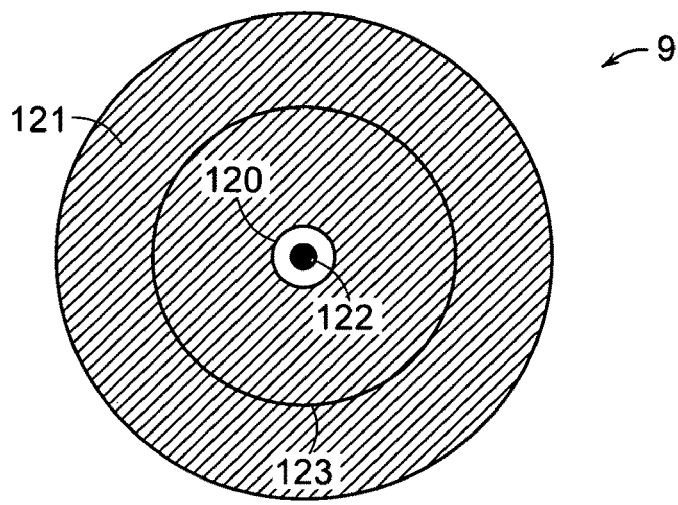
FIG. 3 is a detailed plan view of the spatial filter shown in FIG. 1.

The cw output beam 15 shown for simplicity in FIG. 1 as a collimated beam. By slight movement of the lens 3 along its optical axis, the output beam 15 can be focused onto the surface of the object. This focusing makes the beam 15 convergent toward its focusing point. FIG. 2 illustrates the focused laser projector beam 15 striking the surface of the object 105 at the focusing spot 110. Generally, the object's surface diffusively reflects the incoming beam 15. Because of diffusion, the reflected light 111 is widely spread back toward laser projector 20. As discussed above, a very small portion of this diffusely reflected light 111 gets back through the beam steering mirrors 5 and 6 into the optical feedback subsystem 30.

The returned portion of the diffusely reflected light 111 makes its way toward the beam splitter 4 sharing the same beam path through mirrors 5 and 6 with the projecting beam 15. This reflected light is also termed herein the feedback beam, although it is not converged into a beam in the same way that lenses 2 and 3 create a projected output beam. Part of the returned reflected light reflects as beam 17 from the beam splitter 4 into the optical feedback subsystem 30. The beam splitter 4 decouples the return feedback light beam from the output beam in their shared beam path. Within subsystem 30, the beam 17 further reflects from mirror 7, and is then focused onto the spatial filter 9. The beam 18 transmitted through spatial filter 9 finally enters the high-sensitivity photo detector 10 where it is converted into an electrical signal that corresponds to the intensity of the feedback beam 18.

Typically beam splitter 4 has a transmission-to-reflection ratio from 50:50 to 90:10. The preferred ratio for the present invention is 90:10 because it is characterized by less beam power loss for the laser projection.

The power level of light diffusely reflected back from a typical object material such as plastic or painted metal, returned through the projector's beam steering system, and reflected from beam splitter 4 as the beam 17, is in the range of about 50 to about 500 picowatts of power. The high-sensitivity photo detector 10 can convert such extremely low level of optical power into a corresponding electrical signal. The detector 10 is preferably a photo multiplier tube (PMT).

A substantial problem solved by the TLP 20 for such continuous wave laser light beam interrogation of an object surface is the suppression of excessive (also termed herein "unwanted" or "stray") background light that otherwise makes the optical feedback signal from diffusely reflected surface of the object 105 indistinguishable. (As will be described below, with the LRP 100R invention, the problem of stray light is reduced as compared to the TLP 20 now being described.) Major sources of the excessive background light that enters the feedback subsystem 30 along with the feedback beam 17 include:

1) Part of the beam 16 that diffusely reflects from the beam dump 11 and passes through the beam splitter 4 back into the subsystem 30;
2) Part of the laser beam 13 scattered from the surface of the beam splitter 4 toward the subsystem 30;
3) Part of the laser beam 14 scattered back from the beam steering mirrors 5 and 6; and
4) Part of ambient light illuminating object 105 that diffusely reflects from the surface, reaches laser projector, passes though the beam steering mirrors 5 and 6, reflects from the beam splitter 4, and gets into the optical feedback subsystem 30.

The beam dump 11 is designed to minimize the unwanted background light reflected from it back into the system. Beam dump II is made out of a black material with very low light scattering, for example, Low-Pile Black Velvet available through the McMaster catalog. The distance between the beam dump 11 and the beam splitter 4 is preferably not less than 4 inches. To further reduce reflection back into the system, the beam dump 11 is also preferably tilted by at least 45 degrees with respect to the axis of the beam 16.

The converging lens 8 and the spatial filter 9 provide further suppression of the unwanted excessive background light while at the same time providing effective transmission of the useful feedback beam. Spatial filter 9 is shown in detail in FIG. 3. It is formed by a pinhole 120 in a disk-shaped mask 121 oriented transversely to the optical axis of the feedback beam 17, 18. The lens 8 images the surface of the object 105 illuminated by the projected light beam 15 back onto the spatial filter 9. The rays of the light 111 diffusely reflected from the focused spot 110 that are collected through the beam steering mirrors 5 and 6 and reflected as beam 17 from the beam splitter 4 will be concentrated by the lens 8 into a "point" 122 on the spatial filter 9. The real size of this concentrated point image 122 is diffraction limited; it is typically a spot about 15 to 25 micrometers in diameter, for a focused beam spot on the object 105 having a typical diameter, as noted above, of about 0.4 to 1.0 mm. This image stays at the same location 122 on the spatial filter 9 for any position of the spot 110 on the surface of the object 105, e.g. regardless of the beam steering mirrors angles, because the returned optical feedback light shares its optical path with the projecting laser beam 14, 15.

The image 122 of the point 105 is located in the center of the pinhole 120, hence the optical feedback beam 17 concentrated by the lens 8 into the image 22 will go freely through the spatial filter 9 toward the photo detector 10. Because the excessive background light that goes through the lens 8 is not collimated (it is originated from light scattering surfaces) it is not concentrated within the pinhole 120 but rather blurred over the area 123. Therefore, the spatial filter 9 blocks the excessive background light to distinguish the optical feedback signal from the object surface.

The pinhole 120 is aligned on the optical axis of the beam 17, 18 together with the optical axis of the lens 8 on the light entrance to the PMT 10. The diameter of the pinhole 20 is preferably about 4 times the diameter of the feedback beam at the pinhole (point image 122), in the focal plane of the lens 8. For a focused beam diameter of 15 to 25 micrometers, the pinhole is preferably 100 micrometers in diameter. An increase in the pinhole diameter increases the "field of view" of the object, which allows more ambient light incident on the object to enter the subsystem 30 and the PMT 10, thereby degrading the performance of the system. An increase in the pinhole diameter also allows more stray scattered light within the laser projector to reach the PMT, which also degrades the performance of the system. A decrease in the preferred diameter, on the other hand, creates problems in achieving the proper alignment of the components, particularly as the parts heat and there are thermal shifts, or as the lens 3 is moved to refocus the laser output beam 13, e.g. to accommodate different laser-to-object distances.

The mirror 7 further reduces unwanted background signal from the ambient light. The mirror 7 preferably has its reflective surface covered with a layer that reflects only light with the wavelength of laser 1 (532 nanometers in this embodiment). It therefore works as a band pass filter, reducing the background signal originated by the ambient light. Alternatively, a laser wavelength transmission band pass filter can be placed somewhere into the beam within the subsystem 30.

Figure 4:
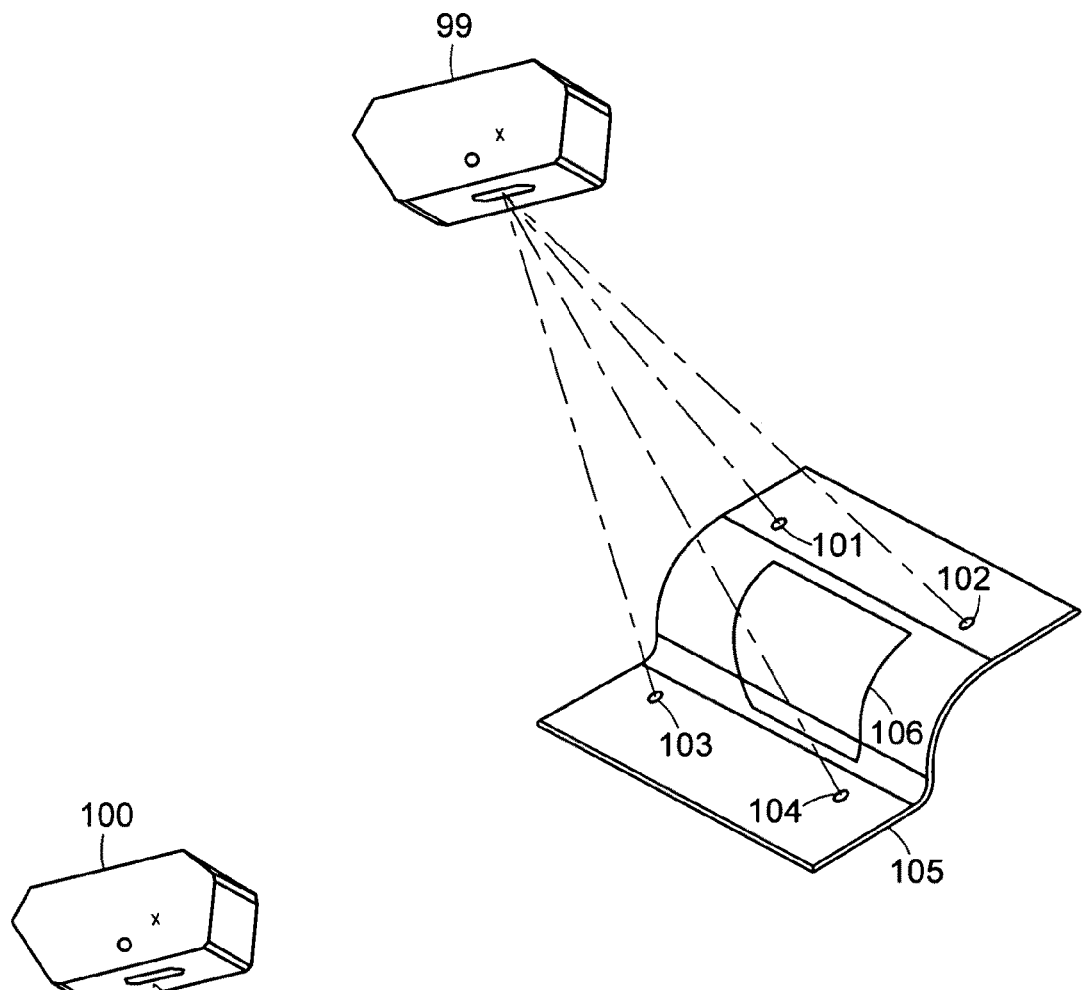
FIG. 4 is a simplified view in perspective of a prior art laser projector scanning a 3D object with retro-reflective targets secured thereon.

FIG. 4 illustrates a prior art method of 3D laser projection—generating a glowing template onto an object for precision placement of component parts in 3D space. Laser projector 99 is arbitrary located in 3D space with respect to the object 105. There are two major steps in this prior art method of laser projection:

Step 1. The laser projector 99 utilizes its optical feedback capabilities and the set of retro-reflective or cooperative targets 101, 102, 103, and 104 as fiducial points to determine projector's location and orientation in 3D space with respect to the object 105. The computation is based on a given set of coordinate data for the targets 101-104 with respect to the object 105. This process referred herein by the phrase "buck into the object's coordinate system".

Step 2. The laser projector utilizes input CAD data for the predetermined projection trajectory for a given object 105 in combination with projector's location data determined in the Step 1. It produces rapidly moving laser beam that strikes the surface of the object 105 precisely following a predetermined, computer controlled trajectory in a repetitive manner. With sufficiently high beam speed and refresh rate, the trajectory of the projected beam on the object appears to human eye as a continuous glowing line 106.

The prior art implementation is well known in the industry. Solutions disclosed in U.S. patents referred above are different in certain aspects but they all rely on use of reference cooperative or retro-reflective targets as fiducial points for bucking into the object's coordinate system. Typically, at least three to six fiducial points are required.

Figure 5:
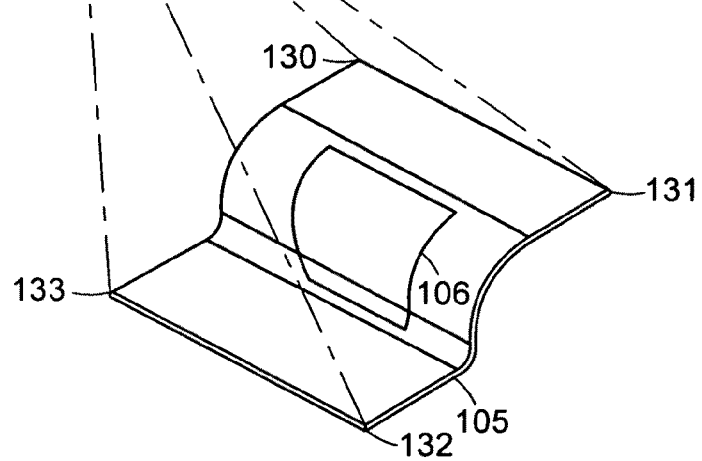
FIG. 5 is a view corresponding to FIG. 4 showing the laser projector of FIG. 1 scanning the same 3D object, but using object feature points as fiducial points.

The present targetless method of laser projection as described with reference to FIGS. 1-15 is illustrated in FIG. 5. There are two major steps in this method of laser projection.

Step 1. The laser projector 100, using the optical components described above with reference to FIGS. 1-3, and its high sensitivity optical feedback capabilities, together with the image processing and computational features of the invention described below, which together constitute the laser projector "apparatus". Laser projector 100 is the TLP 20 shown with an exterior housing. It is capable of scanning object features and obtaining distinctive signal from diffusely reflective conventional surfaces. It uses given set of coordinate data for corners 130-133 of to the object 105 as fiducial points to determine location and orientation of the laser projector 100 in 3D space with respect to the object 105.

Step 2. The laser projector 100 utilizes input CAD data for the predetermined projection trajectory for the object 105 in combination with projector's location data determined in the Step 1. It produces rapidly moving laser beam that strikes the surface of the object 105 precisely following a predetermined, computer controlled trajectory in a repetitive manner. With sufficiently high beam speed and refresh rate, the trajectory of the projected beam on the object appears to human eye as a continuous glowing line 106.

Figure 6:
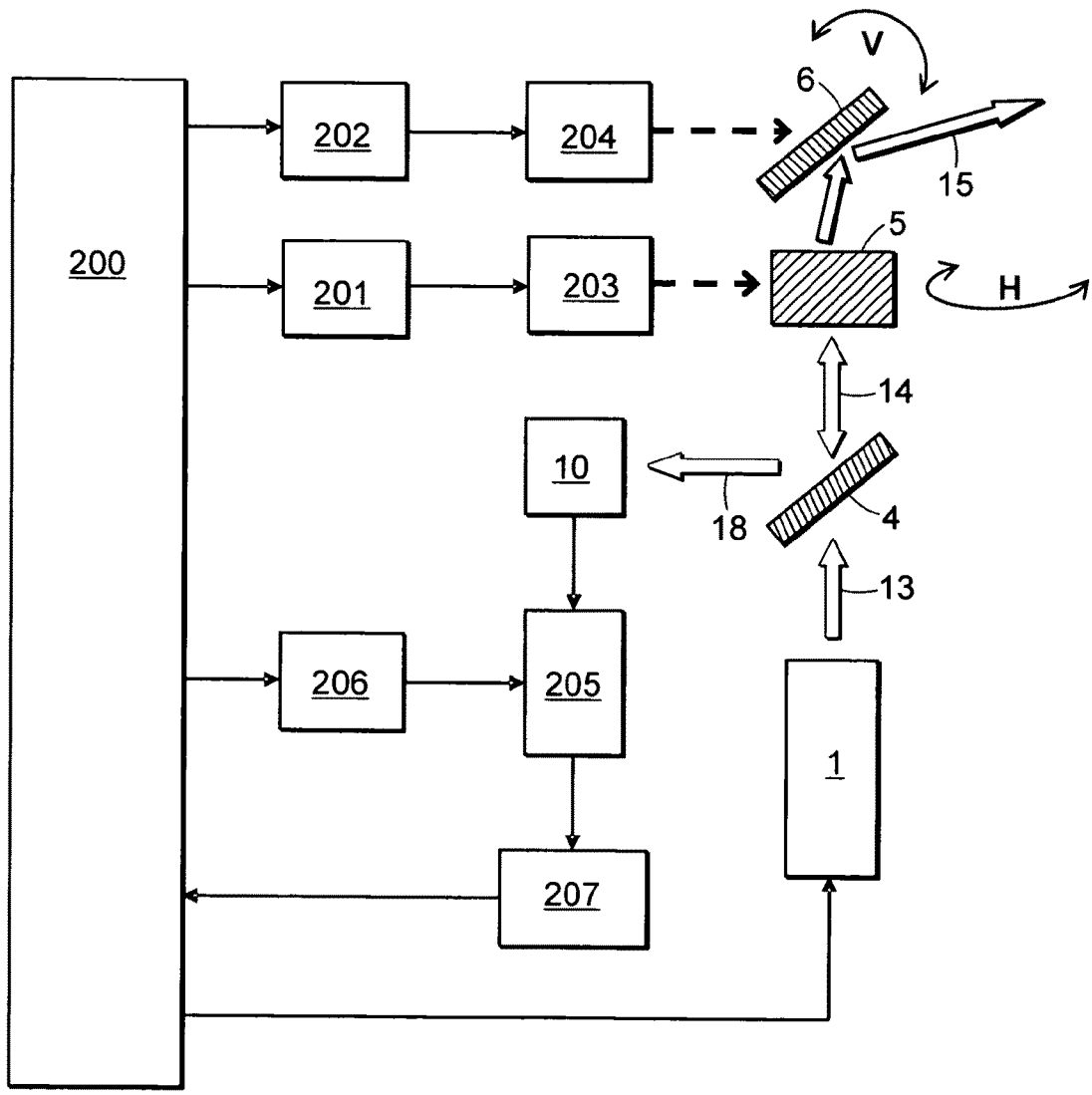
FIG. 6 is a simplified schematic block diagram of the laser projector shown in FIG. 1 illustrating its control and image signal processing electronics.

A functional block diagram of the targetless laser projector 100 shown in FIG. 6.

The projector output beam 15 is being directed toward the object by the pair of orthogonal mirrors 5 and 6 as depicted in FIG. 1. The mirrors 5 and 6 are mounted on the shafts of corresponding galvanometers 203 and 204. The galvanometers are high-precision servo motors containing angular position sensors. Galvanometers that widely used in industrial applications for laser projection are, for example, models 6860 or 6220 made by Cambridge Technology, Inc. Galvanometer 203 rotates mirror 5 to steer the beam 15 in the projector's horizontal (azimuth) plane. The azimuth beam steering angle is denoted as H. Galvanometer 204 rotates mirror 6 to steer the beam 15 in projector's vertical (elevation) plane. The elevation beam steering angle is denoted as V. By steering both mirrors in coordinated manner laser projector can direct output beam toward any point on the object within the angular range of galvanometers. The typical range for H and V angles is ±30 degrees. Galvanometers 203 and 204 are activated by corresponding servo drivers 201 and 202. Each servo driver typically has an integrated 16 bit Digital-to-Analog Converter (DAC) as a front end input interface that obtains command data from a computer 200.

The laser 1 of the laser projector 100 and TPL 20 generates the continuous wave beam 13 is controlled in an ON/OFF mode by the computer 200. (As noted above, this cw operation is not employed in the LRP 100R invention described below which builds on the TLP invention.) This allows the laser projector 100 to generate piece-wise trajectories, or raster scan patterns. As described above, the beam 13 goes through the beam splitter 4. The optical feedback beam 18 from the object 105 via the output beam path, the steering mirrors, and the beam splitter 4, gets onto the high-sensitivity photo detector 10, preferably a photo multiplier tube (PMT).

The output PMT electrical signal goes through an amplifier 205 to the Analog-to-Digital Converter (ADC) 207 to digitize the analog output signal of the amplifier 205. The preferable ADC resolution is 12 to 16 bits. (With the high frequency pulsed laser 1P used in the LRP 100R, the preferable ADC resolution is eight (8) bits.) The ADC 207 output is connected to the digital input of the computer 200.

DAC 206 controls the gain of an amplifier 205 to compensate for changes in the PMT signal strength caused by variations in the optical feedback beam reflected from different kinds of object surfaces. Control of the amplifier 205 gain results in the consistent dynamic range for the input signal of ADC 207. While the present invention operates without retro-reflective targets, should the object nevertheless have a retro-reflector on it, the gain adjustment controls the much stronger return beam signal produced by the target. (Again, while this variation in the gain of the amplifier 205 provides an acceptable level of dynamic range control for the TLP 20, it does not itself provide the dynamic range of 100,000 or more noted above as desirable for a versatile 3D digitizing scanner and projector.

As noted above, in the first step of the laser projection process, the laser projector is aligned to or "bucks into" the object's coordinate system e.g. to determine its location and orientation in 3D space with respect to the object. This is accomplished using a set of reference (fiducial) points. The (x, y, z) coordinates of the reference points are known with respect to the object coordinate system, and they are entered into the memory of the computer 200 as an input data set. This data set will be referred further in this text as the "Tool Data Set," the conventional term in the industry.

In other words, Tool Data Set is a list of coordinates for the reference points:
Reference Point 1: x1, y1, z1;
Reference Point 2: x2, y2, z2;
Reference Point 3: x3, y3, z3;
Reference Point 4: x4, y4, z4;
Reference Point 5: x5, y5, z5;
Reference Point 6: x6, y6, z6;
... [Etc.] ...

Selected object features are used as the reference (or fiducial) points. Object features include sharp and rounded corners, holes, fasteners, "crosses," and the like. For example, FIG. 5 shows use of the sharp corners 130-133 of the object 105 as reference points. To be more specific, each corner vertex is assigned as a reference point, so the Tool Data Set for the case depicted in FIG. 5 includes coordinates of the corners' vertices:
Corner 130: x1, y1, z1;
Corner 131: x2, y2, z2;
Corner 132: x3, y3, z3;
Corner 133: x4, y4, z4;
... [Etc.] ...

If corners are rounded, lines can be computed from edge-detected "shoulder" portions of the corner that are extended computationally to a "virtual" corner meeting point in space that serves as the one reference point for this rounded corner feature. For holes in the object, edge detection and computation can produce a like "virtual" reference point at the calculated center of the hole, e.g. a drilled cylindrical hole.

Figure 7:
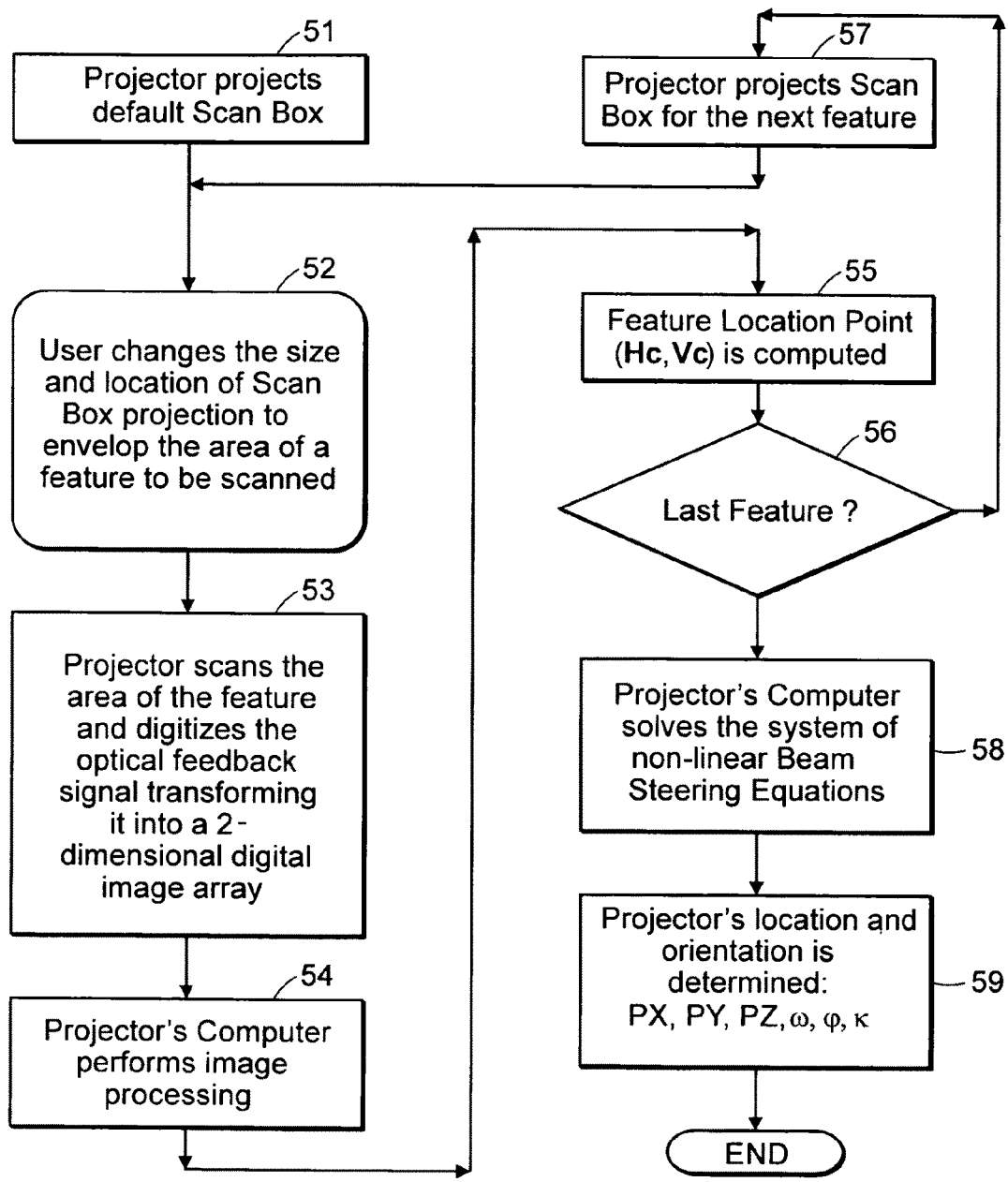
FIG. 7 is a flow chart of the control and processing functions performed by the computer of the laser projector shown in FIGS. 1 and 6 to buck the projector into the coordinate system of the object.
Figure 8:
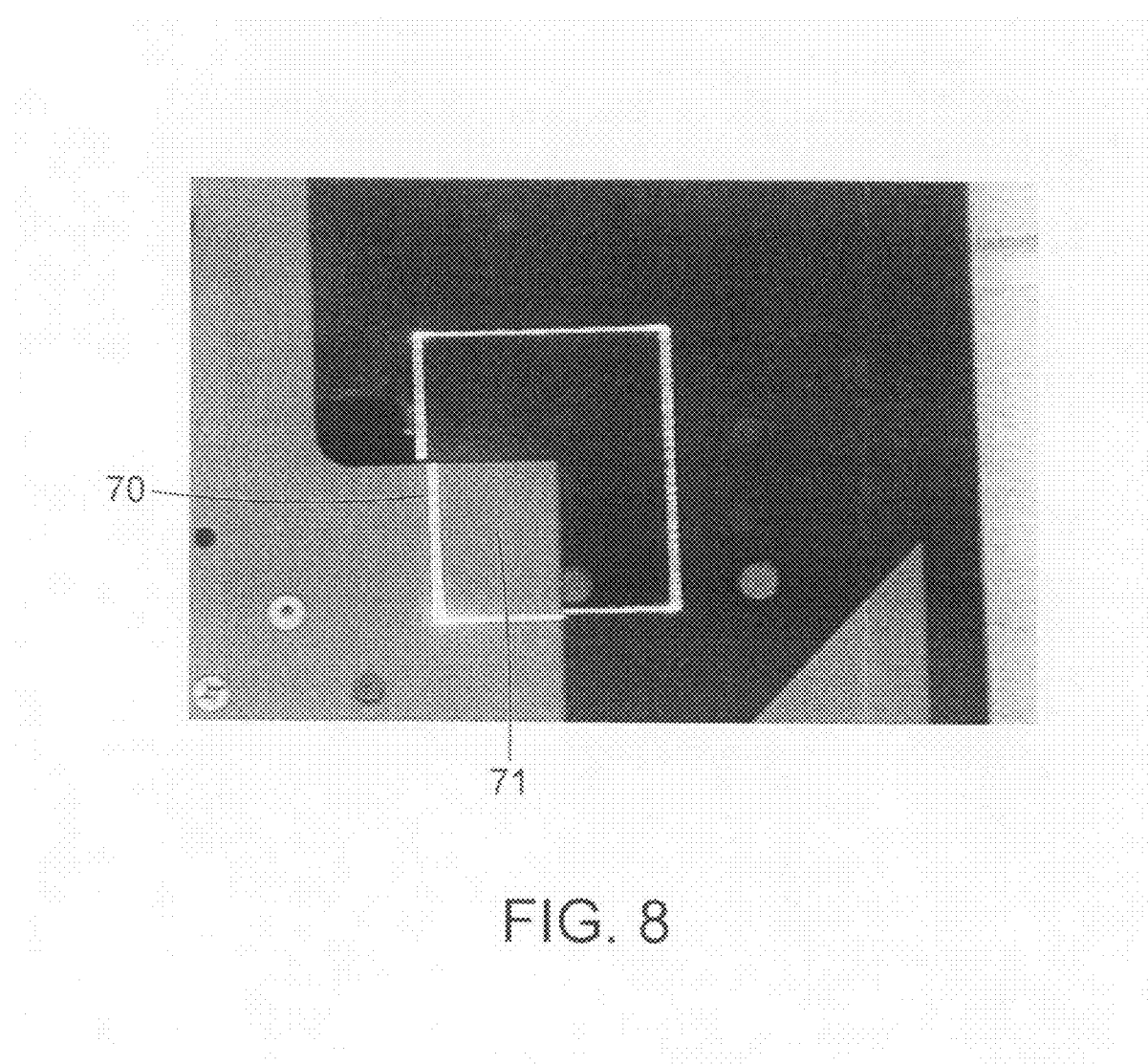
FIG. 8 is an image of a typical object with a scan box projected onto and enclosing an object feature point, a corner.
Figure 9:
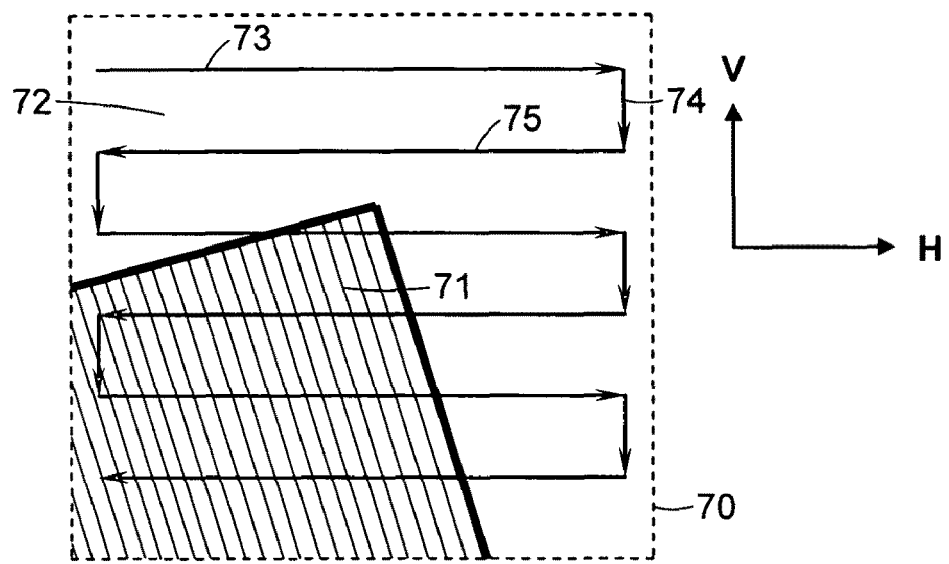
FIGS. 9 and 10 are diagrams showing alternating raster scan patterns and associated scan boxes on an object.

FIG. 7 shows an algorithm for the laser projector "bucking into" the object coordinate system using object features as reference points. At step 51 the projector creates a glowing template referring here as a "scan box". The scan box outlines a rectangular area on the surface of the object were the feature scan will occur. The scan box projected at step 51 has a default location, preferably, in the center of the beam steering range (both, in azimuth and elevation) and a default size, for example, 0.5×0.5 degrees corresponding to approximately 1.5×1.5 inches at 15 feet distance. At step 52 the user changes the size and location of the scan box projected on the surface of the object to enclose the area of the feature needed to be scanned. To control the scan box, the user operates the laser projector through its computer 200 using keyboard or mouse input interface. An example of a typical scan box 70 is shown in FIG. 8. Scan box 70 envelops the area around the feature 71, which has a shape of a corner.

At step 53 projector scans the area of the feature and digitizes the optical feedback signal transforming it into a 2-dimensional digital image array. The preferred scanning method in this invention is raster scanning. The computer 200 generates a scan trajectory as a series of beam steering commands at equal time increments sent to DACs 201 and 202. In the presently preferred implementation of this invention, the feature scan uses a preliminary scan and final scan. Both preliminary and final scans are bi-directional but with different scanning patterns shown schematically in FIGS. 9 and 10, respectively. The preliminary scan of FIG. 9 starts first, and follows the scan pattern 72. The goal of preliminary scan is to determine the optical feedback signal amplitude, and to set up proper gain for amplifier 205 through DAC 206.

Figure 11:
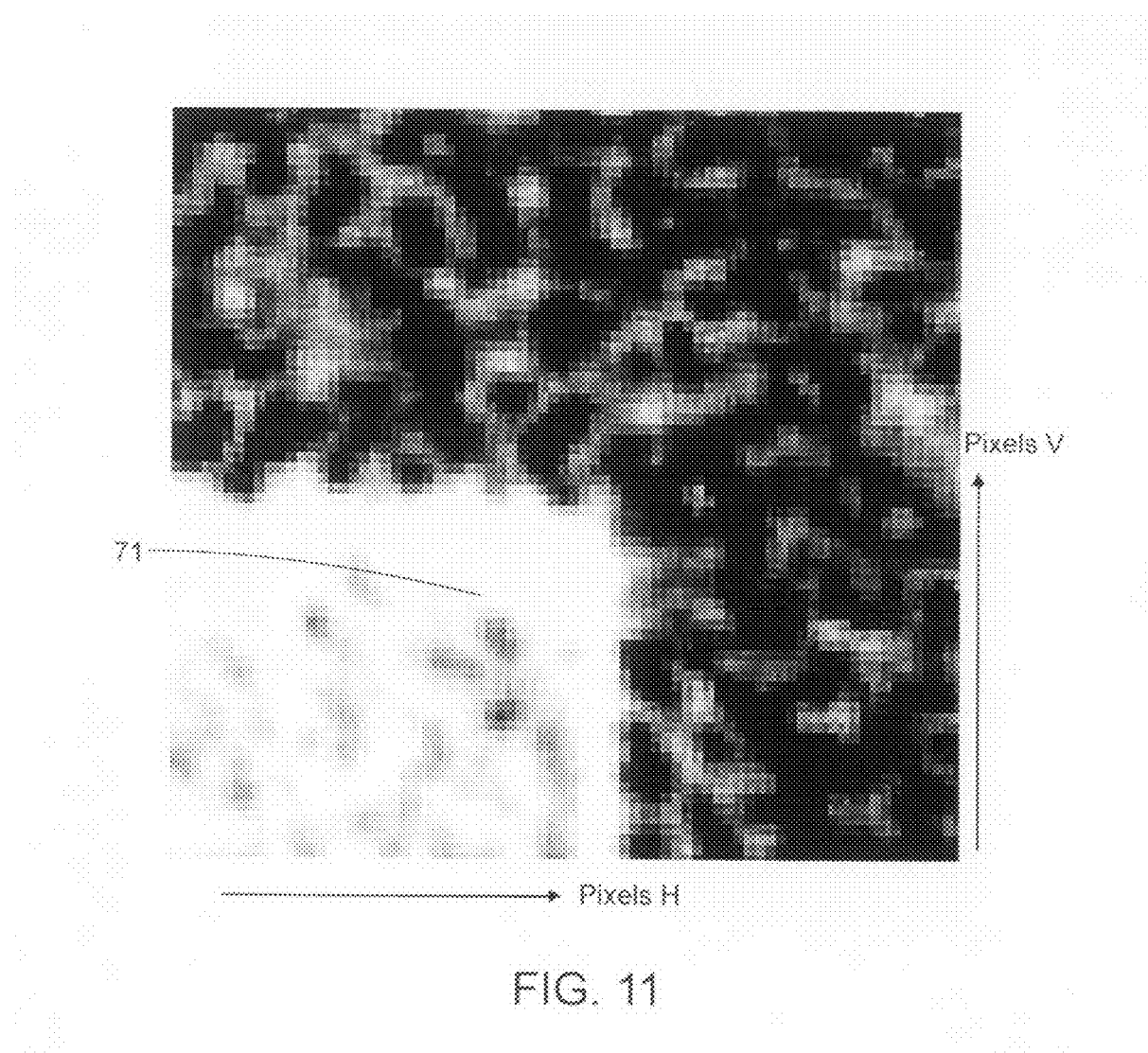
FIG. 11 is an actual pixelized output signal image of a corner feature produced by the laser projector shown in FIGS. 1 and 6.

The preliminary scan begins the following way. Amplifier 205 is set at minimum gain $G_0$ through the DAC 206. The laser beam is steered by the galvanometer 203 (mirror 5) with constant velocity and varying azimuth angle H along the trace line 73. At the end of the line 73 the galvanometer 203 stops, and the galvanometer 204 steers the beam varying elevation angle V along the short path 74. Then the galvanometer 204 stops, and the galvanometer 203 steers the beam along the retrace line 75. The scan process continues in this bi-directional manner covering the whole area that was outlined at step 51 by the scan box 70. During each trace and retrace the galvanometer 203 is driven by the stream of digital commands at equal time increments from computer 200 through the DAC 201. At each time increment computer 200 reads the output of ADC 207, thus sampling the amplified optical feedback signal. In other words, at this step, the laser projector operates in a manner such as that of a digitizing scanner. Computer 200 constructs a 2-dimensional image array row after row, and each row represents digitized optical signal along a trace or retrace scan line. As the result of this scanning, the computer 200 captures a digital "pixelized" image of the feature 71, with horizontal pixels representing sampling in azimuth angle H, and vertical pixels representing sampling in elevation angle V. An example of the "pixelized" image of the corner feature 71 is shown in FIG. 11. It should be understood the metric of the digital image captured by the laser projector is in angular units (radians or degrees).

After completion of preliminary scan, computer 200 analyzes captured digital image and determines the maximum value in the image array. That value corresponds the maximum amplitude of the amplified optical signal $S_{max}$. Then the proper amplifier gain G needed for the final scan is calculated:

$$G = \frac{U}{S_{MAX}} \qquad (1)$$

where U is the input range for the ADC 207.
Next, the amplifier 205 is set to the gain G by computer 200 through the DAC 206, and the final scan begins.

Figure 10:
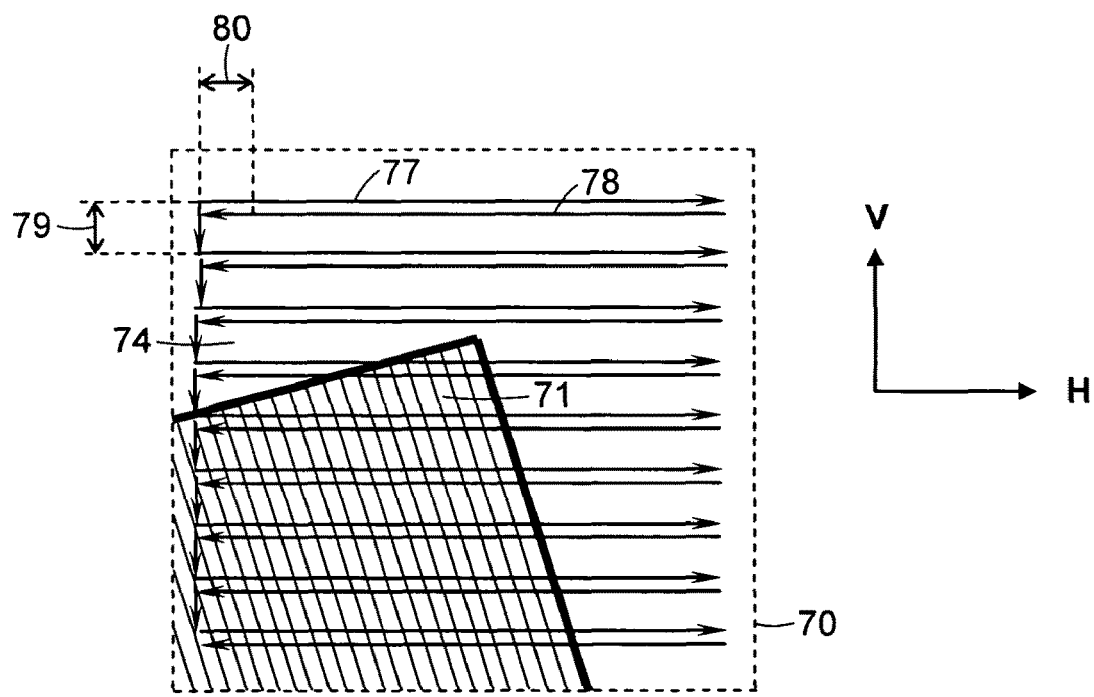

Final scan trajectory is shown in FIG. 10. It follows the bi-directional scan pattern 74. In contrast to the preliminary scan, the final scan trajectory has trace 77 and retrace 78 paths superimposed exactly on the same line (they are shown in FIG. 10 as slightly separated in the vertical direction only for illustration purpose). Otherwise, the process of final scan, galvanometer control, and the optical feedback signal digitizing are the same as described above for preliminary scan. The final scan resolution has to be adequate for the required feature location precision. Typical scan line separation 79 (V pixel size) and the sampling interval 80 (H pixel size) are each 30 to 50 micro radians.

The final scan pattern is significant in the operation of the TPL 20/laser projector 100. When computer 200 drives galvanometer 203 quickly, there is a noticeable lag in the ability of the galvanometer to follow the driving command. The difference between the actual and the commanded position of the galvanometer at the moment of sampling the optical signal brings an offset error to the digitized data. In other words, the output electrical signal representative of the intensity of the feedback light diffusely reflected from a point on the object is not precisely correlated with that point. The data acquired during trace scans is shifted to the left, and the data acquired during retrace scans is shifted to the right. If scan velocity is constant, the offset value is also constant. Actually, the offset value depends not only on the galvanometer lag, but also on the delay in the amplifier 205. Because the lag and delay values are usually unknown, so is the amount of the data offset. However, the absolute value of the offset is the same for trace and retrace—only the sign is opposite. Based on that, the problem of an unknown scan lag is solved in this invention by constructing separately two digital image arrays for all traces and all retraces. Computer 200 constructs each image array in the same manner as described above for the preliminary scan. Therefore, as a result of the final scan, two digital images of the feature are captured by computer 200—a "trace image" and a "retrace image".

Figure 12A:
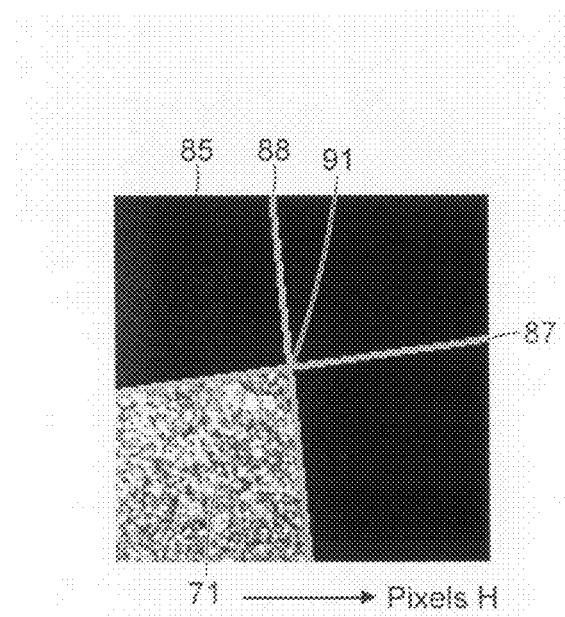
FIGS. 12A and 12B show actual pixelized output signal images of the same corner feature taken in opposite horizontal directions in a raster scan of the type shown in FIG. 10.
Figure 12B:
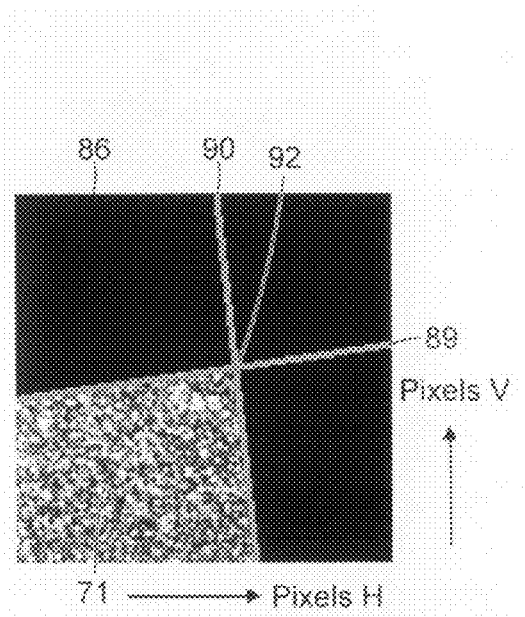

Trace and retrace digital images of the scanned corner feature 71 are shown in FIG. 12. It can be seen that the trace image 85 and the retrace image 86 look the same with exception of some offset between them in horizontal (H) direction. By processing those images separately and finding the feature location for each of them, the real feature location may be found by averaging trace and retrace locations, thereby controlling the error introduced by unknown lag.

Referring back to FIG. 7, at step 54 computer 200 runs image processing routines, separately for trace and retrace images, to detect the scanned feature location in (H,V) space, e.g. elevation and azimuth of its reference point. As it was described above, in the case of a corner, its reference point is its vertex, whether real or virtual. In other words, the vertex location in (H,V) space corresponds the beam steering direction from the projector origin to the vertex.

As the vertex is just the point of intersection of the corner's edges, the computer 200 runs a routine to detect and locate these edges in a digital image. Known methods of digital image processing for video systems, ultrasound scanners, radars and the like are described in technical literature, for example, Gonzales, R. C. and Woods, R. E., *Digital Image Processing*, 2$^{nd}$ ed., Prentice Hall, Upper Saddle River, N.J. (2002) As will be understood by those skilled in the art, image processing can include computer routines to filter noise and speckles in the image, extract pixels that lie along edges, apply image segmentation to select the strongest edge pixels, and to run least square fit yielding final edge line locations. Also, ready-to-use software libraries implementing image processing routines that can be used within the present invention are commercially available from vendors, such as MathWorks in the U.S., or Matrox in Canada. An example of edge lines 87, 88, 89, and 90 detected by digital image processing routine at step 54 is shown in FIG. 12.

At step 55 the line intersection points 91 and 92 for trace and retrace images 85 and 86 are computed. Then the feature location reference point ($H_C$, $V_C$), in angular coordinates with respect to projector's origin, is calculated as follows:

$$H_C = \frac{H_T + H_R}{2} \quad (2)$$

$$V_C = \frac{V_T + V_R}{2} \quad (3)$$

Figure 13A:
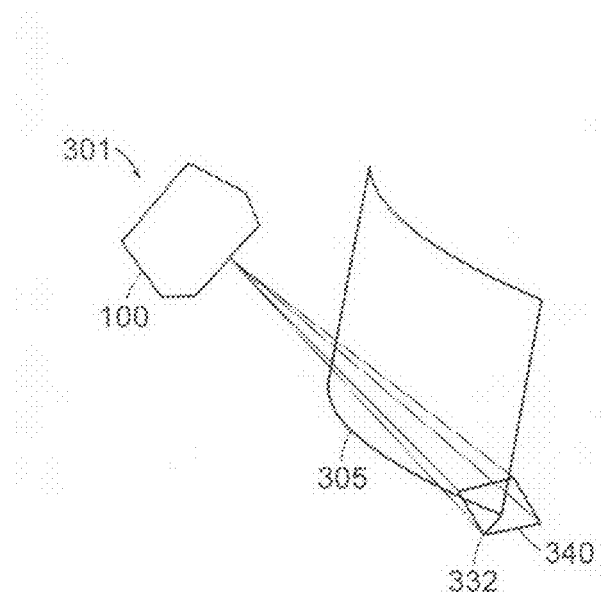
FIGS. 13A and 13B are views of a laser projector operated to detect a corner feature from two different angles with respect to the same object.
Figure 13C:
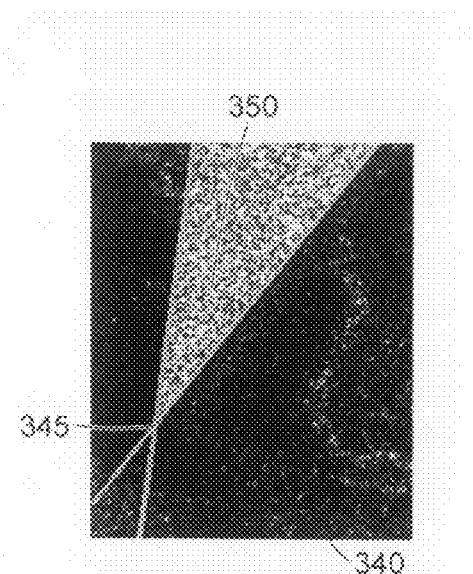
FIGS. 13C and 13D are actual output signal image of the corner feature produced by the operation of the laser projectors shown in FIGS. 13A and 13B, respectively.
Figure 13B:
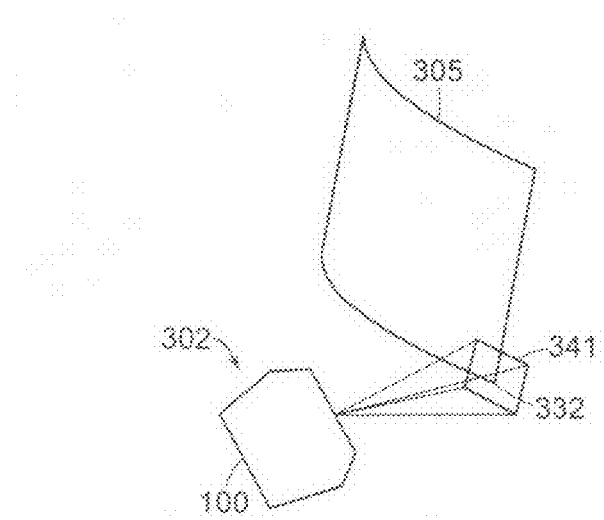
Figure 13D:
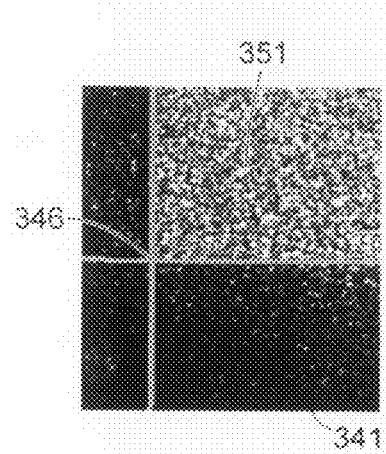
Figure 15:
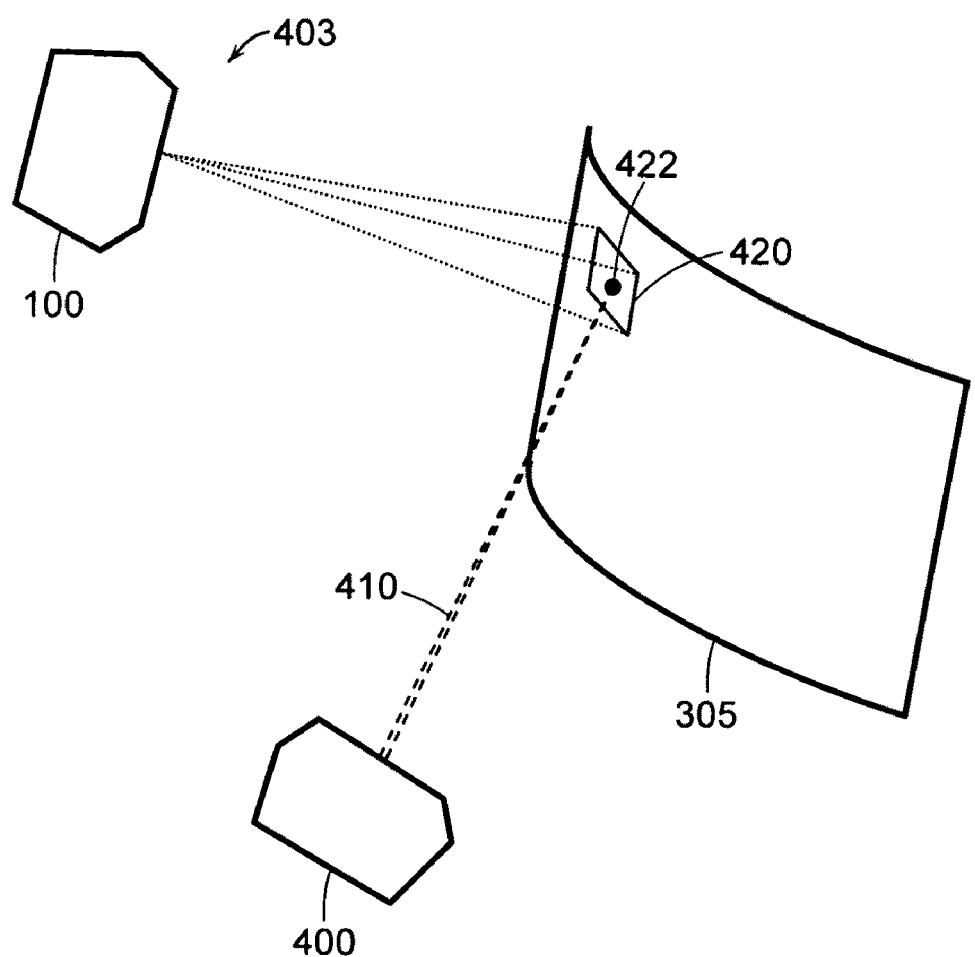
FIG. 15 illustrates an alternative method of operation where a laser spot on an object constitutes the object feature being scanned by the laser projector.

Where:
$H_T$ and $V_T$ are the beam steering angles, azimuth and elevation, of the intersection point 91 (edge lines 87 and 88) found for the trace (T) image;
$H_R$ and $V_R$ are the beam steering angles, azimuth and elevation, of the intersection point 92 (edge lines 89 and 90) found for the re-trace (R) image;

As mentioned above, the features are represented in the tool data set as single reference points. A shape of a feature preferably used in the TLP/20 laser projector 100 has to provide unambiguous detection of its reference point independently of the orientation of the projector 100 with respect to the object in 3D space. An example of a preferred feature shape is a corner. The combination of the scan and image processing methods described for steps 53-54 brings an important performance advantage—the computed intersection point derived from detected edges always corresponds to the vertex of the corner feature, regardless of the projector orientation with respect to the object. This is illustrated in FIGS. 13A and 13B. When laser projector 100 is oriented in position 301 with respect to the object 305 (FIG. 13A) it scans the area 340. In this situation, the detected edges in the scanned image 350 of the corner 332, as shown in FIG. 13C, appear to for an acute angle with respect to each other. When the laser projector 100 is oriented in position 302 with respect to the object 305 (FIG. 13B) it scans the area 341. For this orientation, the detected edges in the scanned image 351 of the corner 332, as shown in FIG. 13D, appears to form a right angle with respect to each other. But in both layouts the intersection points 345 and 346 unambiguously correspond to the vertex of the corner 332, and the computed angular coordinates ($H_C$, $V_C$) will be consistent in both cases with beam steering direction from the projector's origin to the vertex of the corner feature in 3D space.

Another example of a preferred feature shape for TLP is a circular "dot". This shape is characteristic of a wide class of features such as drilled holes, fasteners, etc. Scan and image processing of a dot feature is illustrated in FIGS. 14A-14D. The laser projector 100 is oriented in position 303 with respect to the object 305, as shown in FIG. 14A. It scans the area 360 and captures the digital scan image 365 of the circular dot feature 362. The reference (fiducial) point of the circular dot feature is its center. A dot feature can be included in the Tool Data Set by specifying its center coordinates (x, y, z) with respect to the object coordinate system. As it shown in FIGS. 14B-14D, the shape of the real digital image 365 appears as elliptical for this particular orientation of the laser projector 100 with respect to the object 305. The computer 200 runs a routine to detect the edge 366 of the dot image 365 (FIG. 14C) and to find the center 367 (FIG. 14D). Again, elliptical edge detection and center finding algorithms are well known in the art, and the software libraries implementing required routines are available from Mathworks, Matrox, and other image processing software vendors. The preferred method of separate trace and retrace image processing described above for corners is also fully applicable to dot feature images. The dot feature location point ($H_C$, $V_C$) in angular coordinates with respect to projector's origin can be calculated by averaging trace and retrace image centers similarly to corner's computation using formulas (2). Different projector positions and orientations will result in different ellipticity and orientation of the image 365, but the center of the ellipse will always correspond to the center point of the dot 362, and the computed angular coordinates ($H_C$, $V_C$) will be consistent with beam steering direction from the projector's origin to the center of the dot feature in 3D space.

Referring again to FIG. 7, at step 56 the computer 200 checks if the feature scanned is the last feature in the Tool Data Set list. If it is not, a scan box for the next feature is projected at step 57, and the algorithm returns to step 52. If the last feature in the Tool Data Set has been scanned and processed, the system is ready to complete "bucking in" by finally computing projector's location and orientation in 3D space with respect to the object. At this point computer 200 accumulates a list of angular coordinates for all scanned features:
$H_1$, $V_1$;
$H_2$, $V_2$;
$H_3$, $V_3$;
. . . [Etc.] . . .

The preferred types of features applicable to this invention are not limited by flat corners and dots described above. It should be understood that other features such as 3D corners, 2D and 3D rounded corners, fabricated countersink holes, crosses, square and diamond shaped fasteners, etc. can be used.

At step 58 the set of all computed angles and x, y, z points for the features are used by the computer 200 as data to solve a system of non-linear beam steering equations to compute the location and orientation in 3D space of the laser projector 100 with respect to the coordinate frame of the object (e.g. tool) being scanned. As is well known, there are six projector location and orientation parameters to be computed:

PX, x-coordinate of the projector origin;
PY, y-coordinate of the projector origin;
PZ, z-coordinate of the projector origin;
ω, pitch—projector's rotation around the axis parallel to the X axis of the tool frame and going through projector origin;
φ, yaw—projector's rotation around once rotated Y axis;
κ, roll—projector's rotation around twice rotated Z axis;

Each reference point is associated with two beam steering equations that, in generic form, can be expressed as follows:

$$F(H, V, x, y, z, PX, PY, PZ, \omega, \phi, \kappa)=0; \quad (3)$$

$$G(H, V, x, y, z, PX, PY, PZ, \omega, \phi, \kappa)=0; \quad (4)$$

Where functions F and G, as is well known, are defined by geometry of the beam steering mirror system.

At least three reference points are needed to generate at least six equations in order to compute six unknown parameters (PX, PY, PZ, ω, φ, κ) of projector location and orientation. With more than three reference points the system of equations becomes over-determined and has to be solved using a least-squares method. Suitable particular expressions for the laser projector beam steering equations and solving algorithms are described in detail in the aforementioned U.S. Pat. No. 6,547,397 to Kaufman and Savikovsky, the disclosure of which is incorporated herein by reference.

Once the laser projector's location and orientation in 3D space with respect to the object coordinate frame has been determined, it is ready to project glowing templates on the surface of the object following input CAD data in the form of (x, y, z) list of trajectory points defined in the object coordinate frame. A detailed description of the algorithms used in projector's computer to implement proper projection of glowing templates in 3D space is also given in U.S. Pat. No. 6,547,397.

Another aspect of the TLP described herein is the ability of the targetless laser projector 100 to detect a light spot on an object from another laser source very much the same way it detects a feature of the object. In the exemplary illustration of the embodiment of the invention shown in FIG. 15, an external source 400 directs a laser beam 401 toward the object 305. The laser beam 410 has the same wavelength as the laser wavelength used by the projector 100, preferably green light, 532 nanometers. The laser beam 410 is focused into a static spot 422 on the surface of the object 305. The diameter of the spot 422 is preferably about the same as the diameter of the focused spot that can be produced by the laser projector 100, typically about 0.4-1 mm. The power of the beam 410 is not more than 5 milliwatts to meet safety standards.

As described above, the laser projector 100 is capable of detecting very low level of light as an optical signal reflected from a diffusive surface. The projector 100 scans the area outlined by scan box 420 that contains the spot 422. Using image processing method described above for a dot feature, the projector's computer 200 locates angular coordinates (H, V) for the spot 422. Any appropriate laser system can be used as a source 400, for example, another laser projector, or simply a statically mounted laser with proper power, wavelength, and spot size on the object.

Laser Radar Ranging and Targetless Projection

As detailed below with reference to FIGS. 16-18, the feature detection, reference point determination, processing verification, reverse engineering, and other features and applications of this invention are combined and enhanced with laser "radar" ranging, provided by laser radar projector ("LRP") 100R, which is also referred to herein as the Targetless Laser Radar Projector ("TLRP"). The laser radar projector 100R is a 3D digitizer and projector with performance characteristics far beyond those of the ranging laser projector described in the Kaufman and Savikovsky '397 patent.

Figure 16:
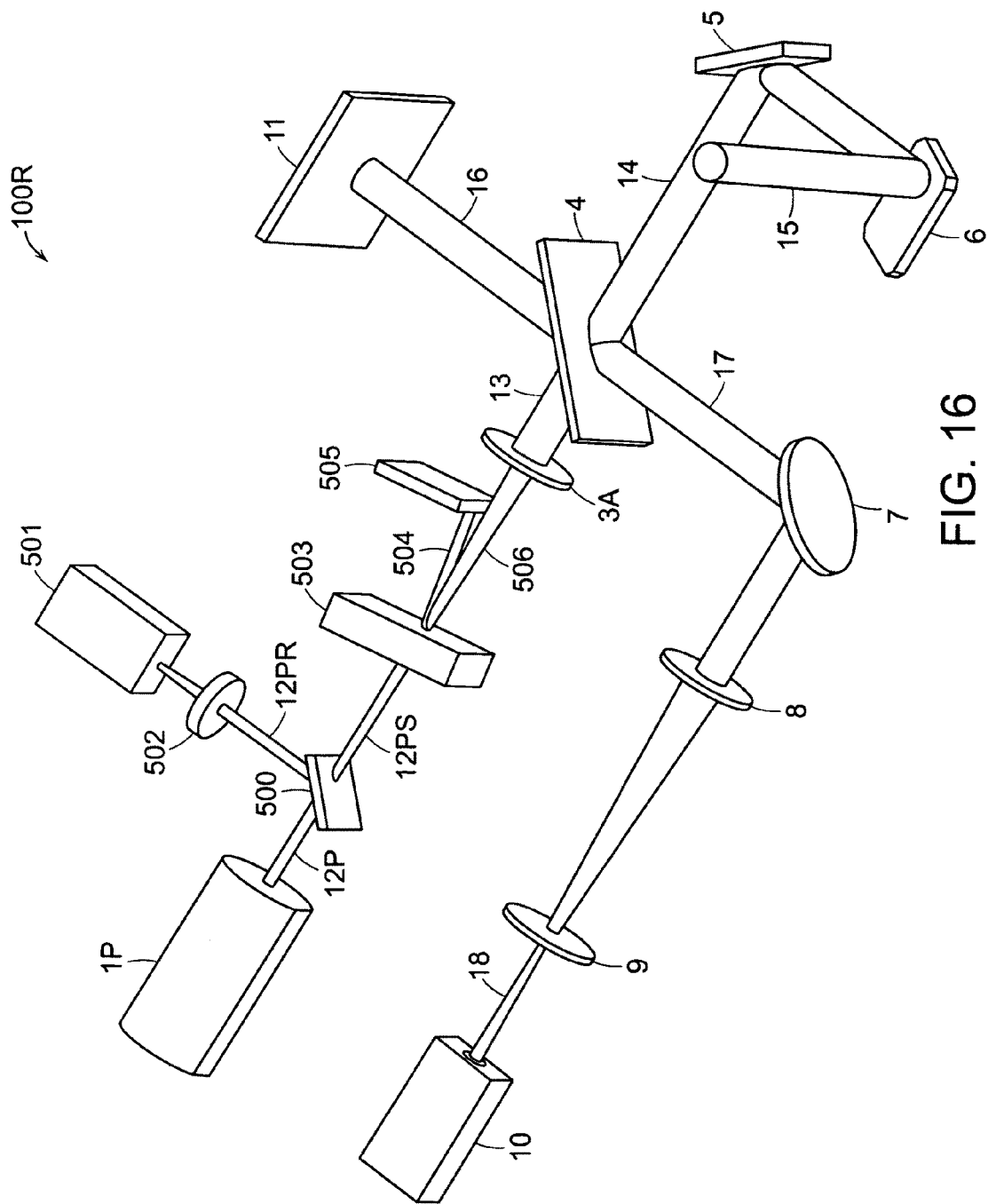
FIG. 16 is a simplified view in perspective corresponding to FIG. 1 of a laser radar projector according to the present invention that can detect features on a scanned object and which can find the range to each scanned point on the object with excellent dynamic range.

FIG. 16 shows the laser radar projector 701 of the present invention. It builds on the "TLP" invention shown in FIG. 1 and described hereinabove with reference to FIGS. 1-15). The LRP 100R as shown in FIG. 16 has added elements as compared to the projection subsystem of the TLP as shown in FIG. 1, which, broadly stated, include a reference channel beam splitter 500, a focusing lens 502, a reference photo detector 501, an acousto-optical modulator 503 and a zero-order beam blocker 505. The beam expanding combination of lenses 2 and 3 shown in FIG. 1 is represented by element 3A in FIG. 16.) Like parts in the FIG. 1 TLP and FIG. 16 LRP are designed with the same part number, or in certain instances, with the same part number primed, or with additional alphabetical notations, to indicate some particular structural or functional differences, such as cw laser 1 and pulsed laser 1P. In addition, the LRP 100R uses a laser light source 1P that is a pulsed ("P") laser (typically a Q-switched laser). In one exemplary form, it produces green light at wavelength of 532 nm, each pulse duration is typically 250-500 picoseconds, and the average power of the laser output is not more than 5 milliwatts, the upper power limit for the class IIIa lasers.

A significant aspect of the LRP 100R is that the repetition rate of the laser pulses is at least 50 kHz, preferably at or near 100 kHz. As will be explained below, such a high repetition rate is important for the quality of the laser projection and the precision with which a scanned surface of one object can be represented as a 3-D digital point cloud.

The laser 1P emits a pulsed output laser beam 12P. The beam splitter plate 500 reflects part of the laser beam 12P toward the lens 502 that concentrates received light onto the reference photo detector 501. Typically the beam splitter 500 only reflects about 1% of the incoming light from the laser 1P. Such a beam splitter plate is of known design. A suitable splitter 500 is produced by Thorlabs under the trade designation "Beam Sampler—Beam Pickoff," part No. BSF.OS-A1. Photo detector 501 is preferably a photodiode capable of detecting sub-nanosecond light pulses. In a preferred form, it typically has a very small light sensitive area, e.g. about 100-200 micrometers in diameter.

The larger "signal" part 12PS of the laser beam 12P, typically about 99%, passes through the beam splitter 500 toward the acousto-optical modulator ("AOM") 503. Acousto-optical modulators are well known in the art of electro-optical and laser systems.

For example, they are described in depth in technical literature, for example, Xu, Jieping and Stroud, Robert, *Acousto-optic Devices: principles, design, and applications*, John Wiley & Sons, Inc., 1992. When a control signal is applied to the AOM 503, it splits the incoming laser beam into the first order beam 506 and the zero order beam 504. The intensity of the first order beam 506 depends on the strength of the control signal: the stronger the signal, the more incoming light is being redirected into the beam 506. When no control signal applied to the AOM 503, all the light passes through it in the direction of the zero order beam 504 and is completely blocked by the plate 505. Therefore, the AOM 503 serves as a beam shutter. Also, by redistributing the laser beam between the zero order and the first order, the AOM 503 plays a role of a variable beam attenuator. In practice, the dynamic range of variable beam attenuation that can be achieved by a typical AOM 503 ranges from 1 up to 300 to 500. (Note that the plate 505 is sufficiently removed from the detection of the return diffusely reflected light by the PMT 10 that light scattering at the plate 505 is not a concern for that detection. Scattering at the splitter 4 and scanning mirrors 5,6 is of much greater concern, and dealt with as described above, and hereinbelow.)

The first order beam 506 further passes through a beam expander/collimator represented by the element 3A, and the expanded beam 13 hits the beam splitter 4. From this point, the beam propagation toward the object of scanning and projection and back to the photo detector 10 is the same as described above in the description of the TLP features.

In accordance with the present invention, the laser beam 12P consists exclusively of light pulses. Each pulse of light emanating by the laser 1P is divided by the beam splitter 500 into two associated pulses: a reference pulse and the signal pulse. The reference pulses of light travel toward the photo detector 501 along beam path 12PR. The signal pulse travels along the propagation path of the first order beam 506, beam 13, beam 14, and beam 15 toward the object through scanning and projection. As with the TLP 20, the light diffusely reflected from the object, propagates back toward the projector, and portions of it end up at the photo detector 10. Therefore, the photo detector 10 captures the signal pulse of light that traveled from the projector toward the object and all the way back. The difference in time between the reference pulse and the signal pulse represents the time needed for the light pulse to travel from the projector to the object and back. That, in accordance with the well-known principle of time-of-flight ranging, allows a calculation of the distance between the projector and the object by multiplying the time difference by the speed of light.

The light pulses emitted by the laser 1P are quite short, and therefore so are the electrical output pulses obtained from the photo detectors 501 and 10. The outgoing optical reference pulses and the associated reference electrical signals form a reference channel, and the outgoing optical signal pulses and the associated diffusely reflected feedback pulses and their associated electrical output pulses form a signal channel. The output pulses are connected to a very wide bandwidth signal conditioning and processing electronics as detailed below, and including computer 200'. Such electronics typically generates a large amount of heat that can disturb stability of the opto-mechanical assembly and, eventually, degrade the precision of the system. This heat problem is addressed by the preferred embodiment of this invention shown in FIG. 17.

Figure 17:
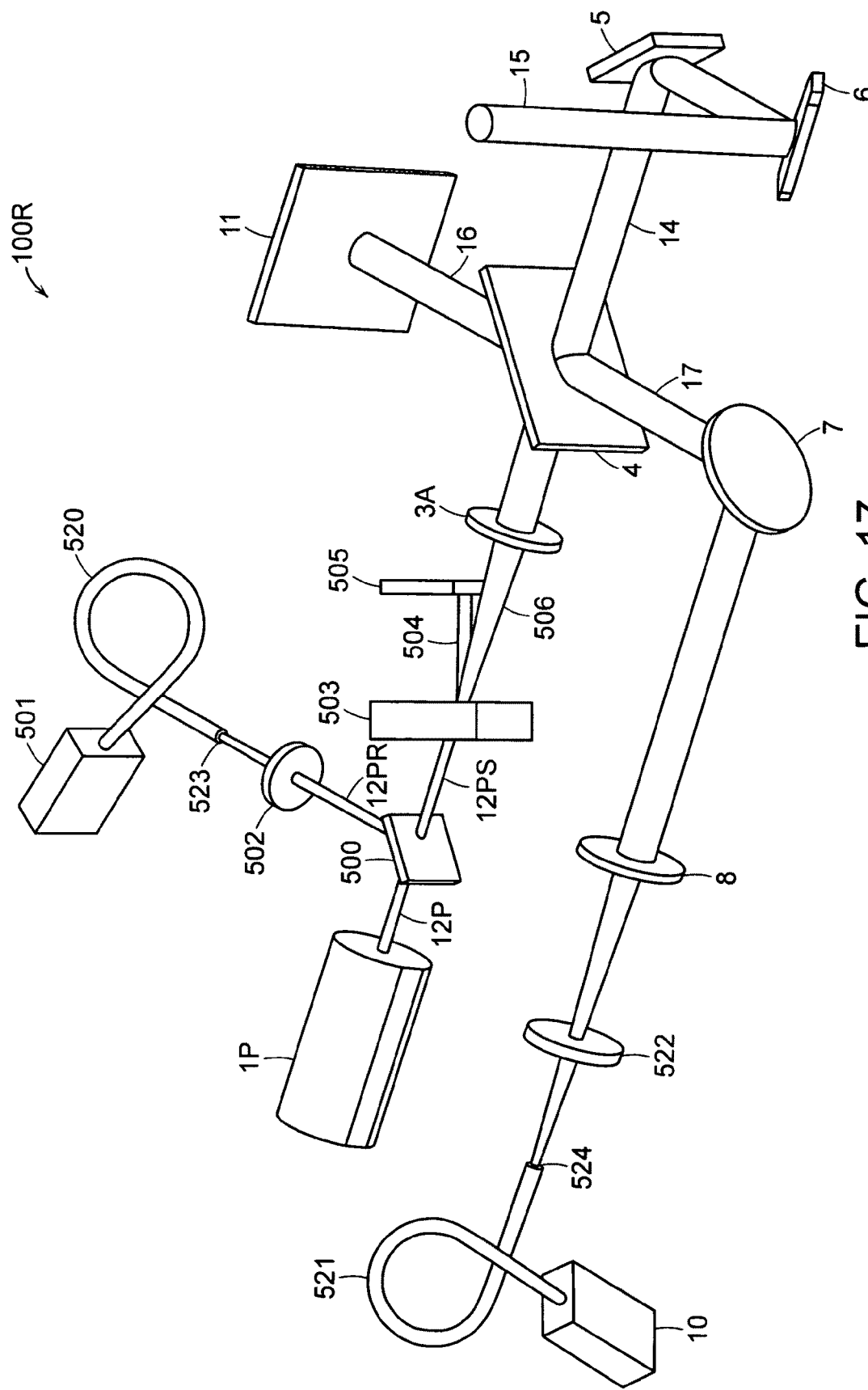
FIG. 17 is a view corresponding to FIG. 16 of a preferred form of the invention using fiber optics for heat isolation and stray light control.
Figure 18:
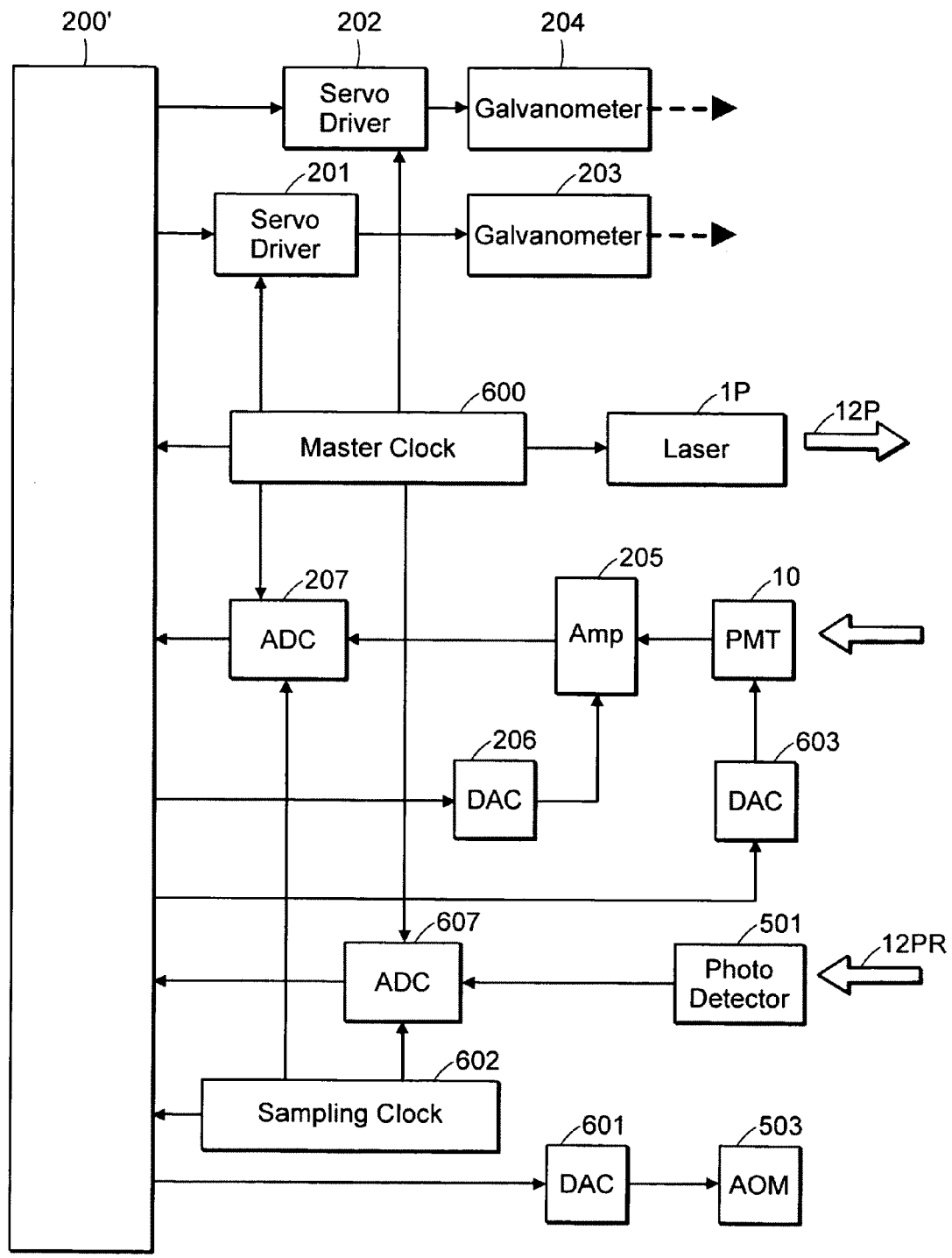
FIG. 18 is a simplified schematic functional block diagram for the laser radar projectors shown in FIGS. 16 and 17.

As shown in FIG. 17, the photo detectors 10 and 501 are separated from the rest of the opto-mechanical system by the optical fiber cables 521 and 520. The fiber cables 520 and 521 are typically multimode fibers with core diameter 50-100 micrometers. The lens 502 concentrates the non-expanded reference laser beam into the inputs 523 of the fiber cable 520. The expanded beam 17 reflected by the mirror 7 is focused into the input 524 of the fiber cable 521 by the lenses 8 and 522. Two lenses 8 and 522 are needed to concentrate a relatively wide beam, typically 15 mm in diameter, into the core of the fiber input 524. It should be understood that two lenses 8 and 522 are presented here as an exemplary embodiment, and they could be replaced by a one lens element, for example, a single aspherical lens.

As described above in connection with the TLP 20, an important aspect of this invention is the suppression of the "unwanted" or "stray" background light. In the TLP system 20, the spatial filter 9 (FIG. 3) containing a pinhole 120, preferably 100 micrometers in diameter, significantly aids in background light suppression. In the preferred embodiment of the LRP 100R as shown in FIG. 17, the function of the stand alone spatial filter 9 is replaced by the core of the fiber cable input 524. The function of this core is exactly the same as the function of the pinhole 120 described above.

That said, it should also be noted that the control of stray light is less key with the LRP 100R than with the TPL 20/LP 100. This is because the diffusely reflected light that reaches the photodetector 10 is time delayed with respect to the scattering produced by the output beam 12P as it is propagated through the LRP for projection. In other words, the detected light pulses are out of synch with the scattering produced by the outgoing pulses associated in time with the reference pulses produced at the photodetector 501. On the other hand, light scattering is strong and if not controlled, can drive the amplifiers to saturation, causing the LRP to fail to detect the return feedback signal.

As with TLP 20, the signal channel photo detector 10 in the LRP 100R has a very high sensitivity to convert extremely low level of optical power into a corresponding electrical signal. The detector 10 is preferably a fast photo multiplier tube (PMT) capable of detecting sub-nanosecond light pulses. As discussed below, it preferably includes a variable power supply that can vary its sensitivity or gain.

The control and signal processing electronics for the TLRP 100R is based on the on the system shown in FIG. 6 for the TLP 20. FIG. 18 shows a functional block diagram using additional elements pertained to the laser radar projector solution and their relation to the components of the TLP system 20.

All functions of control and digital signal processing are performed by the computer 200'. The laser 1P that generates pulses of light is being triggered by a master clock 600 with the frequency typically about 100 kHz. As it described in detail above in connection with the TLP 20, the computer 200' generates a scan trajectory as a series of beam steering commands at equal time increments sent to DACs of the servo drivers 201 and 202. According to the present invention of the TLRP 701, those equal time increments are defined by the master clock 600. The master clock 600 synchronizes stream of position commands from the computer 200 to the galvanometer servo drivers 201 and 202 during both modes of beam steering control—projection or object scan (the TLRP acting as a 3-D digitizing scanner creating a dense 3-D digital point cloud of the object).

When performing the object scan, including ranging and feature detection, the preferred object scanning method of this invention is raster scanning of the general type described hereinabove with respect to the TLP 20/laser projector 100. With the LRP 100R, synchronization between laser pulses and the beam steering commands means that the raster scan pattern consists of separated dots of light that are spatially fixed with respect to each other.

Synchronization between laser pulses and the beam steering commands during projection of a glowing template is a significant aspect of the present TLRP invention. It results a projection trajectory that consists of fixed dots. As the laser projector refreshes the image of a glowing template, it repeats the same trajectory again and again, and it is perceived by a viewer as a steady image, which is necessary to obtain acceptable quality of laser projection. At a given beam steering velocity, the higher the repetition rate of the laser pulses, the smaller the separation between the fixed dots of light in the projection trajectory.

As mentioned above, in accordance with the present LRP invention, the repetition rate of the laser pulses is preferably as high as about 100 kHz. This is because for most applications of laser projection, the separation between the fixed dots would not be acceptable if it exceeds 0.25 inches. At a typical laser projector beam steering velocity of 150 radians per second, and the repetition rate of 100 kHz, the separation of 0.25 inches between dots will be achieved at the distance of 15 feet between the projector and the object, which is quite appropriate for the most applications of laser projection. Decreasing the laser repetition rate while preserving the required separation between the dots, requires decreasing of the projecting speed. That, in its turn causes flicker and degrades the projection quality. Note that scanning is typically conducted at a lower beam scan velocity than in projection. While scanning, closer dot separations, e.g. of 0.010 inch or 0.020 inch at 15 feet projection distance, are typical.

As described above in connection with the TLP 20, the output electrical signal of PMT 10 goes through an amplifier 205 to the ADC 207 to digitize the analog output signal of the PMT. In the case of the LRP 100R, this analog output signal will correspond to the laser pulse, which is typically about 250 to 500 picoseconds in duration.

In order to facilitate the time-of-flight ranging capability, the reference signal, which is also a pulse, 250 to 500 picoseconds in duration, is obtained as an electrical output of the photo detector 501, and it is connected to the ADC 607. Both Analog-to-Digital Converters, 207 and 607, are very fast digitizers, controlled by the sampling clock circuit 602. A typical sampling rate for the present TLRP invention, is about 10 billion samples per second (10 Gigasamples per second). In accordance with the present invention, based on the time-of-flight principle, the reference pulse comes after the signal pulse with the delay equal approximately to the time that is needed for the laser light to travel from the projector to the object and back. For the laser projection applications of the LRP 100R, this distance is not expected to be greater than 100 feet. Accordingly, the maximum time delay between the signal pulse and the reference pulse is going to be not greater than 200 nanoseconds. Meanwhile, for the repetition rate 100 kHz, the time period interval between the current pair of pulses (signal and reference) and the next one is 10 microseconds. As it can be see from FIG. 18, both ADCs, 207 and 607 are gated from the master clock 600 to eliminate "empty" parts of time period intervals from being sampled and processed.

The digital outputs from ADCs 207 and 607 are connected to the computer 200' that digitally processes them to determine the pulse intensity for the signal channel and the time delay between the reference channel pulse and the signal channel pulse. Each channel signal pulse is represented in the computer memory as a sampled and recorded waveform of the pulse. The signal channel pulse intensity values (peak values of the recorded waveforms) are utilized to construct a "pixelized" intensity image for feature detection as described above in detail with respect to the TLP 20 for feature detection. The time delay is used to calculate the distance between the projector and the object by multiplying the time delay by the speed of light. In turn, the time delay itself is determined by the computer 200' as the difference between timing locations of the reference channel pulse waveform and the signal channel pulse waveform with respect to the sampling time clock. Extracting the timing location of the pulse waveform independently of the pulse's amplitude and its offset is well known in the art of radar and ranging systems design. There are well developed methods utilizing correlation with a matched filter and consequent differentiation. As one example, such methods are described by Merrill Scolnik "Introduction to Radar Systems", McGraw-Hill, International Editions, 2002.

As soon as the distance from the projector to the object is calculated, the computer 200' constructs the point cloud of the scanned object utilizing H and V pixel locations in the galvanometer space (as described above in connection with the TLP 20) and the distance data associated with each scan pixel. The data distance has to be valid for each scan pixel in order to obtain a point cloud with high spatial resolution and adequately extract detailed information about scanned 3D objects needed for high precision laser projection. The present TLRP invention solves the substantial problem of obtaining valid signal pulses for all the pixel scan locations.

It does so despite the fact that the strength of the signal pulse returned from the object can vary quite significantly. First the objects themselves have very different surface reflectivity. The variety of objects with different reflectivity in industrial applications ranges from shiny metal surfaces and retro-reflective targets to the black carbon fiber materials. In addition, the intensity of the light captured by the signal channel photo detector varies reciprocally to the squared distance between the projector and the object. Typically, the dynamic range of overall intensity variations related to different objects and distances is in excess of 100,000, and can be as large as about 500,000. In order to overcome this serious obstacle, the present invention has several features.

First, the AOM 503 is used, as described above, to variably reduce the intensity of the outgoing laser pulse, so the signal returned from shiny surfaces would have an intensity, appropriate for the input range of the ADC 207. As it shown in FIG. 18, the AOM 503 is being controlled by a Digital-to-Analog Converter (DAC) 601 controlled by digital commands from the computer 200.

Second, the variable gain amplifier 205 controlled by the DAC 206 helps to mitigate variations in the signal strength, as described above in connection with the TLP 20. Typically, the dynamic range that such amplifier can handle is about 10-20.

Third, the gain of the PMT 10 itself can be adjusted by changing its power source voltage through DAC 603. Typically, the dynamic range achieved by varying the PMT power supply voltage is about 500 to 1000.

By multiplying the dynamic range capabilities of AOM, the variable gain amplifier, and the PMT power source control, the required dynamic range of 500,000, or even more, can be achieved.

In order to obtain valid signals from all the scan pixels, in accordance with this invention, a multi-pass scan algorithm is utilized. It is similar to the one described above in connection with the TLP 20 having a preliminary scan and a final scan. The present LRP 100R sequentially runs several scans in the following manner:

First, the preliminary scan is run the same way as with the TLP 20. The maximum signal strength is thus determined.

Then, the system consequently run a number of scans (passes) covering the same area. At each pass, the only pixels recorded to be valid are ones where if their corresponding signal strength is within the given range for the ADC. Each next pass is being run with the gain approximately twice higher than the previous pass. Other pixels become valid at other passes. After a number of such passes (iterations), almost all the pixels are recorded with valid signal strength and, of coarse, ranging time delay. Typically, about 6 to 8 iterations may be needed to complete the process.

While the invention has been described with reference to the foregoing exemplary embodiments, and certain presently preferred features and embodiments, it will be understood that various modifications and alterations will occur to those skilled in the art from the foregoing detailed description and the accompanying drawings. For example, other known lasers, light suppression implementations, light detectors and electronic signal control and processing can be used. Available photodiodes can be used as a detector. Various other light absorbing materials and arrangements can be used in the projector to control stray scattered light.

While a beam splitter is described as creating a reference beam, it will be understood that other devices and techniques, e.g. using bundled optical fibers and acousto-optical modulators, are known for sampling an optical signal. Depending on the level of dynamic response needed, it is also possible to vary a different combination of optical and electrical signals and vary them to different degrees. Further, while a raster scan of object features is described, other scan patterns and techniques are known and could be used. Still further, while use of the LRP for assembly and assembly verification are described, it will be understood that the invention can be used to guide and verify fabrication steps, including painting and related masking, and the application of numbers, letters and designs whether by painting, related masking, application of decals, or otherwise, as well as fabrication steps involving material processing such as drilled holes and cut edges. It is also contemplated that the feature detection of the present invention can be used for identification, and security applications such as scanning of fingerprints or body parts.

These and other modification and alterations will be apparent to those skilled in the art and are intended to fall within the scope of the appended claims.

What is claimed is:

1. A 3D laser scanner and projection system that can detect features detection on and range distance to points on the surface of an object, comprising:
    a laser projector that projects a pulsed laser light beam on the surface and scans the pulsed output beam along a beam path over the surface where a portion of said output light is diffusely reflected from the surface back to said projector as a feedback signal light beam,
    a first optical signal detector at said laser projector that receives said feedback signal light beam and converts it into a digital image signal that corresponds to the detected feedback signal light, and
    a suppression system that controls stray light against reaching said optical detector that would prevent the detection of said feedback signal light, said projected light beam and said feedback signal light beam associated with a given point on the surface propagating in opposite directions along said beam path;
    a time-of-flight measuring system that calculates the elapsed time of flight and distance traveled of pulses from said laser, to points on the object surface, and back via said signal light feedback beam to said detector; and
    a dynamic range modulator that adjusts the operation of said 3D laser scanner and projection system in response to the light reflective characteristics of the object being scanned and projected upon.

2. The 3D laser scanner and projection system of claim 1 wherein said time of flight measurement system includes a beam splitter located in said beam path that divides said projected pulsed laser light beam into a reference beam portion and a signal beam portion, and a second reference optical detector that converts said reference beam portion into a corresponding electrical reference signal.

3. The 3D laser scanner and projection system of claim 2 wherein said time of flight measurement system further includes a lens that focuses said reference beam portion onto said second reference optical detector.

4. The 3D laser scanner and projection system of claim 2 wherein said time of flight measuring system further comprises a computer that compares said digital image signals with the corresponding electrical reference signal to produce a measurement of the distance from said laser projector to the object surface that produces said feedback signal light beam.

5. The 3D laser scanner and projection system of claim 4 wherein said time of fight measurement system further comprises an electronic circuit that samples said reference beam signal, and said digital image signal at a rate sufficient to provide accurate values for said elapsed time of flight and the intensity of said feedback signal light beam.

6. The 3D laser scanner and projection system of claim 5 wherein said pulsed laser beam is pulsed at at least 50 kHz and sampling occurs at at least 5 gigasamples per second.

7. The 3D laser scanner and projection system of claim 5 further comprising a clock that synchronizes the operation of said laser, said sampling circuit, said computer, and said scanning.

8. The 3D laser scanner and projection system of claim 1 wherein said dynamic range variation is on the order of at least 100,000.

9. The 3D laser scanner and projection system of claim 8 wherein said dynamic variation range is near 500,000.

10. The 3D laser scanner and projection system of claim 1 wherein said dynamic range modulator includes an acousto-optical modulator located in said pulsed output beam and operable to vary the intensity of said pulsed output beam over a range from 1 to 300 to 500.

11. The 3D laser scanner and projection system of claim 10 wherein said acousto-optical modulator splits said pulsed output beam into a first order beam and a zero order beam, where said first order beam is scanned on said object and said zero order beam is suppressed.

12. The 3D laser scanner and projection system of claim 11 wherein said dynamic range modulator further includes a variable gain amplifier of said digital image signal output by said first optical signal detector.

13. The 3D laser scanner and projection system of claim 12 wherein said dynamic range modulator further includes a variable power supply for said first optical signal detector that varies its dynamic response to said received feedback signal light beam.

14. The 3D laser scanner and projection system of any of claims 4-7 wherein said first optical signal detector and said second reference signal detector are optically coupled to said system by optical fibers that thermally isolate said detectors from heat produced by said computer.

15. The 3D laser scanner and projection system of claim 1 wherein said light suppression system comprises a spatial light filter that admits said feedback light beam to said photodetector while substantially blocking stray light, and said spatial filter comprises an optical fiber with a central light-conducting core aligned with said optical detector and a converging lens that brings said feedback light beam to a focus at one end of said central light receiving core.

16. The laser light projection system of claim 1 wherein said light suppression system further comprises a light dump that eliminates the split portion of said output light beam that is not projected onto the surface.

17. The laser projection system of claim 1 wherein said computer controls said scanning and processes said digital image.

18. The laser projection system of claim 17 wherein said computer directs said scanning to produce a scan box glowing template.

19. The laser projection system of claim 18 wherein said computer controls said scanning as an iterated raster scanning over all or a selected portion of said object to obtain valid 3D and related light information for substantially all scan pixels.

20. The laser light projection system of claim 19 wherein said light suppression system comprises a beam splitter located in said beam path that decouples said output light beam from said feedback light beam.

* * * * *